(12) United States Patent
Stamler et al.

(10) Patent No.: US 6,352,709 B1
(45) Date of Patent: *Mar. 5, 2002

(54) LOCALIZED USE OF NITRIC OXIDE-ADDUCTS TO PREVENT INTERNAL TISSUE DAMAGE

(75) Inventors: Jonathan S. Stamler, Boston; Joseph Loscalzo, Dover, both of MA (US); John D. Folts, Madison, WI (US)

(73) Assignee: NitroMed, Inc., Bedford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/661,190

(22) Filed: Sep. 13, 2000

Related U.S. Application Data

(60) Division of application No. 09/433,550, filed on Nov. 4, 1999, now Pat. No. 6,174,539, which is a division of application No. 08/460,465, filed on Jun. 2, 1995, now Pat. No. 6,087,479, which is a continuation-in-part of application No. 08/123,331, filed on Sep. 17, 1993, now abandoned.

(51) Int. Cl.[7] .......................... A61F 2/00; A61L 15/00; A61K 9/14; A61K 9/00
(52) U.S. Cl. .................. 424/426; 424/444; 424/486; 424/423; 424/400
(58) Field of Search .............................. 424/422, 423, 424/608, 428, 93.21, 93.1; 514/44, 12

(56) References Cited

U.S. PATENT DOCUMENTS

| | | |
|---|---|---|
| 5,071,649 A | 12/1991 | Hunter et al. |
| 5,385,937 A | 1/1995 | Stamler et al. |
| 5,405,919 A | 4/1995 | Keefer et al. |
| 5,482,925 A | 1/1996 | Hutsell |
| 5,525,357 A | 6/1996 | Keefer et al. |
| 5,536,241 A | 7/1996 | Zapol |
| 5,800,385 A | 9/1998 | Demopulos |
| 5,858,017 A | 1/1999 | Demopulos |
| 5,860,950 A | 1/1999 | Demopulos |
| 6,087,479 A | * 7/2000 | Stamler et al. |
| 6,171,232 B1 | * 1/2001 | Papandreou et al. |
| 6,174,539 B1 | * 1/2001 | Stamler et al. |

FOREIGN PATENT DOCUMENTS

| | | |
|---|---|---|
| CA | 2106105 | 3/1995 |
| WO | WO96/19233 | 6/1996 |

OTHER PUBLICATIONS

Cohen et al, "Intracoronary Cocktail Infusion during Rotational Ablation: Safety and Efficacy," Abstract Presented at Transcatheter Cardiovascular Therapeutics, Feb. 22–26, 1995.

Stamler et al, Proc. Natl. Acad. Sci. USA, 89(1):444–448 (1992).

EPO Communication for EP 94 92 9143 (Sep. 20, 1999).

Paape et al, Federation Proceedings, 44(3):449 (1985).

(List continued on next page.)

Primary Examiner—Thurman K. Page
Assistant Examiner—Isis Ghali
(74) Attorney, Agent, or Firm—Hale and Dorr LLP

(57) ABSTRACT

A method for preventing adverse effects associated with the use of a medical device in a patient by introducing into the patient a device of which at least a portion includes a prophylactic or therapeutic amount of a nitric oxide adduct. The nitric oxide adduct can be present in a matrix coating on a surface of the medical device; can be coated per se on a surface of the medical device; can be directly or indirectly bound to reactive sites on a surface of the medical device; or at least a portion of the medical device can be formed of a material, such as a polymer, which includes the nitric oxide adduct. Also disclosed is a method for preventing adverse effects associated with the use of a medical device in a patient by introducing the device during a medical procedure and before or during said procedure locally administering a nitric oxide adduct to the site of contact of said device with any internal tissue.

50 Claims, 11 Drawing Sheets

OTHER PUBLICATIONS

Simon et al, Arteriosclerosis and Thrombosis, 13(6):791–799 (Jun. 1993).
Hollman et al, Circulation, 68(4):725–732 (1983).
Nishimura et al, Am. J. Physiol., 261(1):H15–H21 (1991).
Sullivan et al, Thromb. Haemostasis, 44(2):76–80 (1980).
Dembinska–Kiec et al, Int. J. Tiss. React., 15(2):55–64 (1993).
Darius et al, J. Cardiovasc. Pharmacol., 6(1):115–121 (1984).
Nishikawa et al, J. Pharmacol. Exp. Ther., 220(1):183–190 (1982).
Kolansky et al, Cardiovasc. Clin. 23:277–291 (1992).
Loeb et al, Thromb. Res., 54(5):477–486 (1989).
Ignarro, FASEB Journal, 3:31–36 (1989).

* cited by examiner

PORCINE CORONARY MODEL:
PROTOCOL

14 NORMOCHOLESTEROLEMIC PIGS

↓

BALLOON INJURY OF RCA AND LCx

↓ pS-BSA OR pS-NO-BSA THROUGH
PERFORATED PERFUSION BALLOON FOR 15 MINUTES

↓

ANGIOGRAPHY AND PLATELET cGMP AT 6 MINUTES

↓

ANGIOGRAPHY AND PATHOLOGIC ANALYSIS
AT 4 WEEKS (9 PIGS)

FIG.8

LOCALIZED USE OF NITRIC OXIDE-ADDUCTS TO PREVENT INTERNAL TISSUE DAMAGE

RELATED APPLICATIONS

This application is a divisional of U.S. application Ser. No. 09/433,550 filed Nov. 4, 1999, allowed, now U.S. Pat. No. 6,174,539 which is divisional of U.S. application Ser. No. 08/460,465, filed Jun. 2, 1995, issued as U.S. Pat. No. 6,087,479, which is a continuation-in-part of U.S. application Ser. No. 08/123,331, filed Sep. 17, 1993, now abandoned.

FIELD OF THE INVENTION

This invention relates to the use of medical devices and to the treatment of damaged vasculature. More particularly, the invention relates to the use of medical devices which are inserted into a patient wherein at least a portion of the device includes a surface which exposes and delivers a form of nitric oxide to vascular surfaces with which it comes in contact. Alternatively the invention relates to the field of preventing the adverse effects which result from medical procedures which involve the use of such a medical device and which include administering a source of nitric oxide to the cite of vasculature contact of such medical devices.

BACKGROUND OF THE INVENTION

The vascular endothelium participates in many homeostatic mechanisms important for the regulation of vascular tone and the prevention of thrombosis. A primary mediator of these functions is endothelium-derived relaxing factor (EDRF). First described in 1980 by Furchgott and Zawadzki (Furchgott and Zawadzki, Nature (Lond.). 288:373–376, 1980) EDRF is either nitric oxide (Moncada et al., Pharmacol Rev. 43:109–142, 1991.) (NO) or a closely related NO-containing molecule (Myers et al., Nature (Lond.), 345:161–163, 1990).

Removal of the endothelium is a potent stimulus for neointimal proliferation, a common mechanism underlying the restenosis of atherosclerotic vessels after balloon angioplasty. (Liu et al., Circulation, 79:1374–1387, 1989); (Fems et al., Science, 253:1129–1132, 1991). Nitric oxide dilates blood vessels (Vallance et al., Lancet, 2:997–1000, 1989) inhibits platelet activation and adhesion (Radomski et al., Br. J Pharmacol, 92:181–187, 1987) and, in vitro, nitric oxide limits the proliferation of vascular smooth muscle cells (Garg et al., J. Clin. Invest., 83:1774–1777, 1986). Similarly, in animal models, suppression of platelet-derived mitogens decreases intimal proliferation (Fems et al., Science, 253:1129–1132, 1991). The potential importance of endothelium-derived nitric oxide in the control of arterial remodeling after injury is further supported by recent preliminary reports in humans suggesting that systemic NO donors reduce angiographic restenosis six months after balloon angioplasty (The ACCORD Study Investigators, J. Am. Coll. Cardiol. 23:59A. (Abstr.), 1994).

Biologic thiols react readily with NO (probably as $N_2O_3$ or NO) under physiologic conditions to form stable, biologically active S-nitrosothiol species (Stamler et al., Proc. Natl. Acad. Sci. U S A., 89:444–448, 1992). S-nitrosothiols exhibit EDRF-like activity in vitro and in viva, including vasodilation (Myers et al., Nature (Lond.), 345:161–163, 1990) and platelet inhibition via a cyclic 3',5'-guanosine monophosphate (cGMP)-dependent mechanism (Loscalzo, J. Clin. Invest., 76:703–708, 1985); (Keaney et al., J. Clin. Invest., 91:1582–1589, 1993).

Over the past two decades, much research effort has been directed towards the development of medical devices and machines that are used in a wide variety of clinical settings to maintain the vital physiological functions of a patient. For example, such devices as catheters, prosthetic heart valves, arteriovenous shunts and stents are used extensively in the treatment of cardiac and other diseases.

However, platelet deposition on artificial surfaces severely limits the clinical usefulness of such devices. Forbes et al., Brit. Med. Bull. 34(2):201–207, 1978; Sheppeck et al., Blood, 78(3):673–680, 1991. For example, exposure of blood to artificial surfaces frequently leads to serious thromboembolic complications in patients with artificial heart valves, synthetic grafts and other prosthetic devices, and in patients undergoing external circulation, including cardiopulmonary bypass and hemodialysis. Salzman, Phil. Trans. R. Soc. Lond., B294:389–398, 1981.

The normal endothelium which lines blood vessels is uniquely and completely compatible with blood. Endothelial cells initiate metabolic processes, like the secretion of prostacyclin and endothelium-derived relaxing factor (EDRF), which actively discourage platelet deposition and thrombus formation in vessel walls. No material has been developed that matches the blood-compatible surface of the endothelium. In fact, in the presence of blood and plasma proteins, artificial surfaces are an ideal setting for platelet deposition (Salzman et al., supra, 1981). Exposure of blood to an artificial surface initiates reactions that lead to clotting or platelet adhesion and aggregation. Within seconds of blood contact, the artificial surface becomes coated with a layer of plasma proteins which serves as a new surface to which platelets readily adhere, become activated, and greatly accelerate thrombus formation (Forbes et al., supra, 1978).

This creates problems in the use of artificial materials at the microvascular level, where the ratio of vessel surface area to blood volume is high (Sheppeck et al., supra). For example, thromboembolism is still the most serious complication following prosthetic heart valve implantation, despite changes in design and materials used. In fact, the incidence of detectable thromboembolism can be as high as 50%, depending on the valve design and construction (Forbes et al.). Further, cardiopulmonary support systems used during cardiac surgery are responsible for many of the undesirable hemostatic consequences of such surgery (Bick, Semin. Thromb. Hemost. 3:59–82, 1976). Thrombosis is also a significant problem in the use of prosthetic blood vessels, arteriovenous shunts, and intravenous or intraarterial catheters.

Conventional methods for preventing thrombus formation on artificial surfaces have a limited effect on the interaction between blood and artificial surfaces. For example, in cardiopulmonary bypass and hemodialysis heparin. has little effect, and the only platelet reactions inhibited by anticoagulants are those induced by thrombin. In fact, it seems that heparin actually enhances the aggregation of platelets (Salzman et al., J. Clin. Invest., 65:64, 1980). To further complicate matters, heparin when given systemically, can accelerate hemorrhage, already a frequent complication of cardiac surgery.

Attempts to inhibit platelet deposit on artificial surfaces involve systemic administration of aspirin, dipyridamole, and sulfinpyrazone. While these have some effect in preventing thromboembolism when given with oral anticoagulants, serious adverse effects can result. Blood loss is significantly increased in bypass or hemodialysis patients following administration of aspirin (Torosian et al., Ann.

*Intern. Med.* 89:325–328, 1978). In addition, the effect of aspirin and similarly acting drugs is not promptly reversible, which is essential during cardiopulmonary bypass. Finally, agents such as aspirin, which depress platelet function by inhibiting cyclo-oxygenase, may block platelet aggregation, but they do not prevent the adhesion of platelets to artificial surfaces (Salzman et al., supra, 1981).

Despite considerable efforts to develop non-thrombogenic materials, no synthetic material has been created that is free from this effect. In addition, the use of anticoagulant and platelet-inhibiting agents has been less than satisfactory in preventing adverse consequences resulting from the interaction between blood and artificial surfaces. Consequently, a significant need exists for the development of additional methods for preventing platelet deposition and thrombus formation on artificial surfaces.

In the same manner as artificial surfaces, damaged arterial surfaces within the vascular system are also highly susceptible to thrombus formation. The normal, undamaged endothelium prevents thrombus formation by secreting a number of protective substances, such as endothelium-derived relaxing factor (EDRF), which prevents blood clotting primarily by inhibiting the activity of platelets. Disease states such as atherosclerosis and hyperhomocysteinemia cause damage to the endothelial lining, resulting in vascular obstruction and a reduction in the substances necessary to inhibit blood clotting. Thus, abnormal platelet deposition resulting in thrombosis is much more likely to occur in vessels in which endothelial damage has occurred. While systemic agents have been used to prevent coagulation and inhibit platelet function, a need exists for a means by which a damaged vessel can be treated directly to prevent thrombus formation.

Balloon arterial injury results in endothelial denudation and subsequent regrowth of dysfunctional endothelium (Saville, *Analyst*, 83:670–672, 1958) that may contribute to the local smooth muscle cell proliferation and extracellular matrix production that result in reocclusion of the arterial lumen.

Reported work on platelet aggregation has demonstrated the effect of nitric oxide adducts on the inhibition of platelet-to-platelet aggregation as a specific stage in clot formation that relates to their common interaction with each other.

SUMMARY OF THE INVENTION

Toward arriving at the present invention, the inventors hypothesized that local delivery of an EDRF-like species to restore or replace the deficiency in EDRF noted with dysfunctional endothelium will modulate the effects of vascular injury and reduce intimal proliferation following injury. The observations that form the basis of this invention relate to the active deposition of platelets on non-platelet tissue beds rather than platelet-to-platelet aggregation.

In accordance with an aspect of the present invention, there is provided a process and product for preventing adverse effects associated with the use of a medical device in a patient wherein at least a portion of the device includes a nitric oxide adduct. Such adverse effects include but are not limited to platelet adhesion and/or thrombus formation when the medical device is used in a blood vessel. As known in the art, platelet adhesion and subsequent platelet activation may result in the blockage of blood vessels particularly after procedures involving use of a medical device for removing blockages such as those often referred to as the phenomenon of restenosis. The medical device can be used elsewhere, such as for example, in patients having cancer of the gastrointestinal tract in the Sphincter of Oddi where indwelling stents (e.g., a Palmaz-Schatz stent, J&J, New Brunswick, N.J.) are placed to maintain patency of the lumen. They are also used in patients having cancer of the esophagus to support the airway opening.

The medical device or instrument of the invention can be, for example, a catheter, prosthetic heart valve, synthetic vessel graft, stent (e.g., Palmaz-Schatz stent), arteriovenous shunt, artificial heart, intubation tubes, airways and the like.

As noted above, in this aspect the device is provided a nitric oxide adduct. Thus, for example, (i) all or a portion of the medical device may be coated with a nitric oxide adduct, either as the coating per se or in a coating matrix; (ii) all or a portion of the medical device may be produced from a material which includes a nitric oxide adduct, for example, a polymer which has admixed therewith a nitric oxide adduct or which includes as pendent groups or grafts one or more of such nitric oxide adducts; or (iii) all or a portion of the tissue-contacting surfaces of the medical device may be derivated with the nitric oxide adduct.

In the first embodiment of the above aspect, coatings can be of synthetic or natural matrices, e.g. fibrin or acetate-based polymers, mixtures of polymers or copolymers, respectively. Preferably they are bioresorbable or biodegradable matrices. Such matrices can also provide for metered or sustained release of the nitric oxide adduct. The device surfaces can be substituted with or the coating mixture can further include other medicaments, such as anticoagulants and the like.

In the next embodiment of this aspect, nitric oxide adducts are incorporated into the body of a device which is formed of a biodegradable or bioresorbable material. Thus, intact nitric oxide adduct is released over a sustained period of the resorption or degradation of the body of the device.

In the embodiment relating to the derivatization of an artificial surface, such as of a medical device or instrument with a nitric oxide adduct, the artificial surfaces may be composed of organic materials or a composite of organic and inorganic materials. Examples of such materials include but are not limited to synthetic polymers or copolymers containing nitric oxide adducts, gold or coated metal surfaces upon which a functionalized monolayer containing the nitric oxide adduct is adsorbed, or synthetic polymeric materials or proteins which are blended with nitric oxide adducts.

Another principal aspect of the invention relates to a medical device comprising an instrument suitable for introduction into a patient of which at least a portion comprises a nitric oxide adduct. As with respect to the above method, (i) all or a portion of the medical device may be coated with a nitric oxide adduct, either as the coating per se or in a coating matrix; (ii) all or a portion of the medical device may be produced from a material which includes a nitric oxide adduct, for example, a polymer which has admixed therewith a nitric oxide adduct or which includes as pendent groups or grafts one or more of such nitric oxide adducts; or (iii) all or a portion of the tissue-contacting surfaces of the medical device may be derivated with the nitric oxide adduct.

Again, the medical device or instrument of the invention can be, for example, a catheter, prosthetic heart valve, synthetic vessel graft, stent, arteriovenous shunt, artificial heart, intubation tube and airways and the like.

Another principal aspect of the invention relates to a method for treating a damaged blood vessel surface or other injured tissue by locally administering a nitric oxide adduct to the site of the damaged blood vessel. Such damage may result from the use of a medical device in an invasive procedure. Thus, for example, in treating vasculature blocked, for example by angioplasty, damage can result to the blood vessel. Such damage may be treated by use of a nitric oxide adduct. In addition to repair of the damaged tissue, such treatment can also be used to prevent and/or alleviate and/or delay reocclusions, for example. restenosis. Preferably, all or most of the damaged area is coated with the nitric oxide adduct per se or in a pharmaceutically acceptable carrier or excipient which serves as a coating matrix. This coating matrix can be of a liquid, gel or semisolid consistency. The nitric oxide adduct can be applied in combination with other therapeutic agents, such as anti-thrombogenic agents. The carrier or matrix can be made of or include agents which provide for metered or sustained release of the therapeutic agents. Nitric oxide adducts which are preferred for use in this aspect are mono-or poly-nitrosylated proteins, particularly polynitrosated albumin or polymers or aggregates thereof. The albumin is preferably human or bovine, including humanized bovine serum albumin.

The localized, time-related, presence of nitric oxide adducts administered in a physiologically effective form is efficacious in diminishing, deterring or preventing vascular damage after or as a result of instrumental intervention, such as angioplasty, catheterization or the introduction of a stent (e.g., Palmaz-Schatz stent) or other indwelling medical device.

Local administration of a stable nitric oxide adduct inhibits neointimal proliferation and platelet deposition following vascular arterial balloon injury. This strategy for the local delivery of a long-lived NO adduct is useful for the treatment of vascular injury following angioplasty.

Typical nitric oxide adducts include nitroglycerin, sodium nitroprusside, S-nitroso-proteins, S-nitrosothiols, long carbon-chain lipophilic S-nitrosothiols, S-nitroso-dithiols, iron-nitrosyl compounds, thionitrates, thionitrites, sydnonimines, furoxans, organic nitrates, and nitrosated amino acids.

Particularly preferred is the localized use of nitroso-proteins, particularly those which do not elicit any significant immune response. An example of such a nitroso-protein which does not elicit any significant immune response is a mono- or poly-nitrosated albumin. Such nitrosylated albumins, particularly the polynitrosylated albumins, can be present as polymeric chains or three dimensional aggregates where the polynitrosylated albumin is the monomeric unit. The albumin of the monomeric unit can be a functional subunit of full-length native albumin or can be an albumin to which has been attached an additional moiety, such as a polypeptide, which can aid, for example, in localization. The aggregates are multiple inter adherent monomeric units which can optionally be linked by disulfide bridges. Additionally devices which have been substituted or coated with nitroso-protein have the unique property that they can be dried and stored.

An additional particularly unique aspect of the invention is that this contemplates "recharging" the coating that is applied to a device, such as a catheter or other tubing as considered above, by infusing a nitric oxide donor to a previously coated surface. For example, an S-nitroso-protein such as S-nitroso albumin will lose its potency in vivo as the NO group is metabolized, leaving underivatized albumin. However, it has been recognized by the inventors that the surface coating can be "recharged" by infusing an NO donor such as nitroprusside. This principal is demonstrated by the experiments reported in Example 2 in which nitroprusside is mixed with albumin engendering subsequent protection against platelet deposition.

Another aspect of the invention is related to the derivatization of an articial surface with a nitric oxide adduct for preventing the deposit of platelets and for preventing thrombus formation on the artificial surface. The artificial surfaces may be composed of organic materials or a composite of organic and inorganic materials. Examples of such materials include but are not limited to synthetic polymers or copolymers containing nitric oxide adducts, gold or gold coated metal surfaces upon which a functionalized monolayer containing the nitric oxide adduct is adsorbed, or synthetic polymeric materials or proteins which are blended with nitric oxide adducts.

The invention also relates to a method and product for administering a nitric oxide adduct in combination with one or more anti-thrombogenic agents. Such agents include heparin, warfarin, hirudin and its analogs, aspirin, indomethacin, dipyridamole, prostacyclin, prostaglandin $E_1$, sulfinpyrazone, phenothiazines (such as chlorpromazine or trifluperazine) RGD (arginine-glycine-aspartic acid) peptide or RGD peptide mimetics, (See Nicholson et al., Thromb. Res., 62:567–578, 1991), agents that block platelet glycoprotein IIb–IIIa receptors (such as C-7E3), ticlopidine or the thienopyridine known as clopidogrel.

Other therapeutic agents can also be included in the coating or linked to reactive sites in or on the body of the device. Examples of these include monoclonal antibodies directed towards certain epitopes/ligands such as platelet glycoprotein IIb/IIIa receptor or cell adhesion molecules such as the CD-18 complex of the integrins or PECAM-1; fragments of recombinant human proteins eg, albumin; pegylated proteins; anti-sense molecules; viral vectors designed as vehicles to deliver certain genes or nucleoside targeting drugs.

BRIEF DESCRIPTION OF THE FIGURES

The invention will now be further described by reference to a brief description of each of the Figures, but in no way are a limitation of the scope of the invention.

FIG. 8 is a flow chart illustrating the protocol of Example 4 which measured the effect on balloon-induced injury of pS-NO-BSA or pS-BSA in porcine coronary artery.

DETAILED DESCRIPTION OF THE INVENTION

Figure 1A:
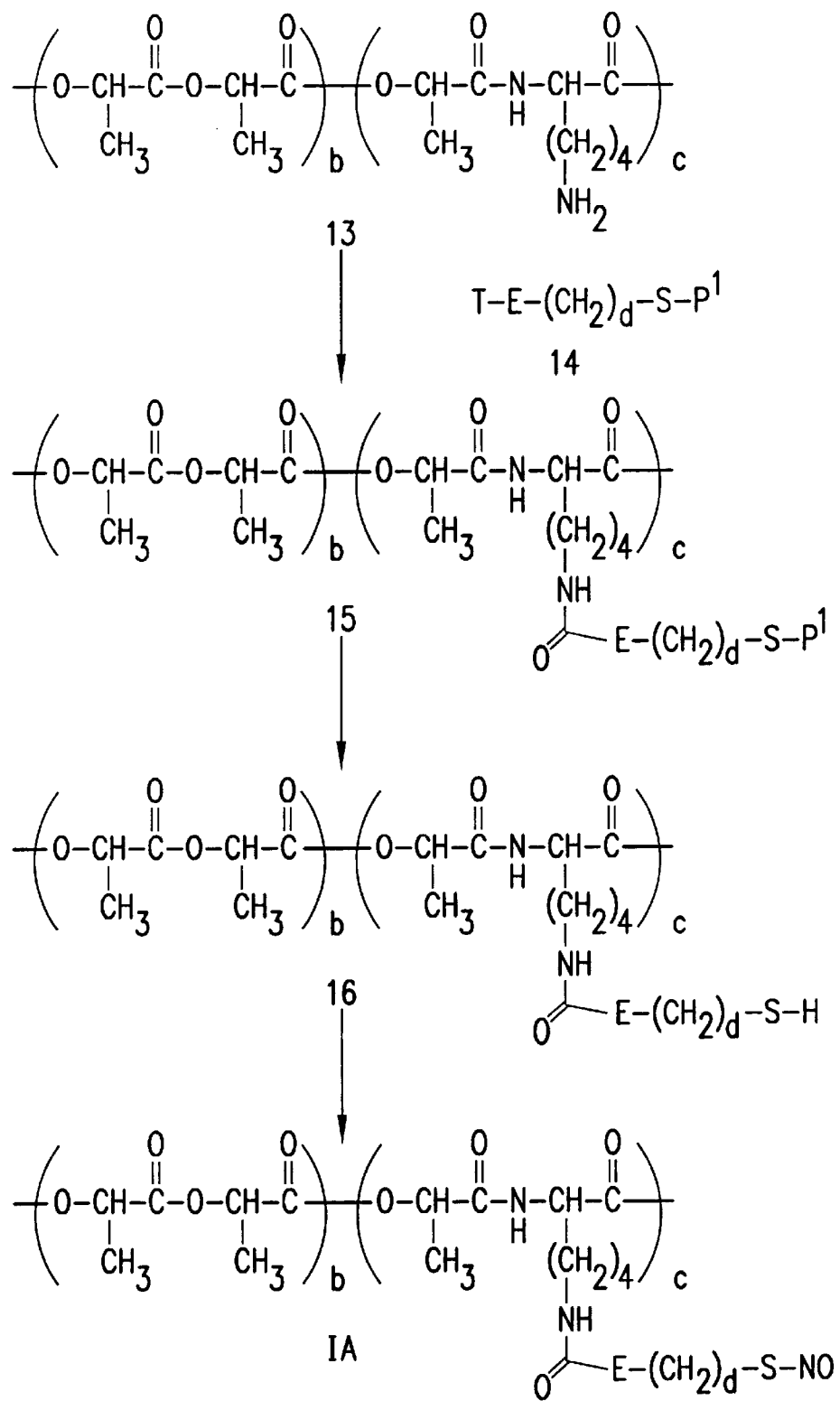
FIG. 1A is a synthetic scheme for the preparation of a nitrosothiol incorporated on to the $\epsilon$-amino group of a copolymer comprised of poly-L-lactic acid-co-lysine.

The invention will now be described in more detail with respect to numerous embodiments and examples in support thereof.

The term "artificial surface" refers to any synthetic material contained in a device or apparatus that is in contact with blood, blood products or components, vasculature, or other tissue.

The term "platelet adhesion" refers to the contact of a platelet with a foreign surface, e.g. collagen, artificial surface or device.

The term "platelet aggregation" refers to the adhesion of one or more platelets to each other. Platelet aggregation is commonly referred to in the context of generalized atherosclerosis, not with respect to platelet adhesion on vasculature damaged as a result of physical insult during a medical procedure.

The term "restenosis" refers to the recurrent narrowing of a blood vessel, usually several months after an injurious insult and as a result of neointimal proliferation.

The term "passivation" refers to the coating of a surface which thereby renders the surface non-reactive.

The term "reendothelialization" refers to the proliferation, migration and spreading of endothelial cells over a surface area which is denuded of endothelial cells, e.g., the surface of a damaged blood vessel.

The term "platelet activation" refers either to the change in conformation (shape) of a cell, expression of cell surface proteins (e.g., the IIb/IIIa receptor complex, loss of GPIb surface protein), secretion of platelet derived factors (e.g., serotonin, growth factors).

The term "lower alkyl" as used herein refers to a branched or straight chain alkyl groups comprising one to ten carbon atoms, including methyl, ethyl, propyl, isopropyl, n-butyl, t-butyl, neopentyl and the like.

The term "alkoxy" as used herein refers to $R_{20}O$-wherein $R_{20}$ is lower alkyl as defined above. Representative examples of alkoxy groups include methoxy, ethoxy, t-butoxy and the like.

The term "alkoxyalkyl" as used herein refers to an alkoxy group as previously defined appended to an alkyl group as previously defined. Examples of alkoxyalkyl include, but are not limited to, methoxymethyl, methoxyethyl, isopropoxymethyl and the like.

The term "amino" as used herein refers to —$NH_2$.

The term "dialkylamino" as used herein refers to $R_{22}R_{23}N$— wherein $R_{22}$ and $R_{23}$ are independently selected from lower alkyl, for example dimethylamino, diethylamino, methyl propylamino and the like.

The term "nitro" as used herein refers to the group —$NO_2$.

The term "nitroso" as used herein refers to the group —NO.

The term "hydroxyl" or "hydroxy" as used herein refers to the group —OH.

The term "cyano" as used herein refers to the group —CN.

The term "carbomoyl" as used herein refers to $H_2N$—C(O)O—.

The term N,N-dialkylcarbomoyl as used herein refers to $R_{22}R_{23}N$—C(O)O— wherein $R_{22}$ and $R_{23}$ are independently selected from lower alkyl, for example dimethylamino, diethylamino, methyl propylamino, and the like.

The term N-alkylcarbamoyl as used herein refers to $R_{22}HN$—C(O)O— wherein $R_{22}$ is selected from lower alkyl, for example methylamino, ethylamino, propylamino, and the like.

The term "aryl" as used herein refers to a mono- or bicyclic carbocyclic ring system having one or two aromatic rings including, but not limited to, phenyl, naphthyl, tetrahydronaphthyl, indanyl, indenyl, and the like. Aryl groups (including bicyclic aryl groups) can be unsubstituted or substituted with one, two or three substituents independently selected from lower alkyl, haloalkyl, alkoxy, amino, alkylamino, dialkylamino, hydroxy, halo, and nitro. In addition, substituted aryl groups include tetrafluorophenyl and pentafluorophenyl.

The term "arylthio" as used herein refers to $R_{24}S$— wherein $R_{24}$ is selected from aryl.

The term "alkanoyl" as used herein refers to $R_{22}C(O)$— wherein $R_{22}$ is selected from lower alkyl.

The term "carboxyl" as used herein refers to —COOH.

The term "guanidino" as used herein refers to $H_2N$—C(=NH)NH—.

The term "arylalkyl" as used herein refers to a lower alkyl radical to which is appended an aryl group. Representative arylalkyl groups include benzyl, phenylethyl, hydroxybenzyl, fluorobenzyl, fluorophenylethyl and the like.

The term "cycloalkyl" as used herein refers to an alicyclic group comprising from 3 to 7 carbon atoms including, but not limited to, cyclopropyl, cyclobutyl, cyclopentyl, cyclohexyl and the like.

The term "halogen" or "halo" as used herein refers to I, Br, Cl, or F. The term "haloalkyl" as used herein refers to a lower alkyl radical, as defined above, bearing at least one halogen substituent, for example, chloromethyl, fluoroethyl or trifluoromethyl and the like.

The term "heteroaryl" as used herein refers to a mono-bycyclic ring system containing one or two aromatic rings and containing at least one nitrogen, oxygen, or sulfur in an aromatic ring. Heteroaryl groups (including bicyclic heteroaryl groups) can be unsubstituted or substituted with one, two, or three substituents independently selected from lower alkyl, haloalkyl, alkoxy, amino, alkylamino, dialkylamino, hydroxy, halo and nitro. Examples of heteroaryl groups include not limited to pyridine, pyrazine, pyrimidine, pyridazine, pyrazole, triazole, thiazole, isothiazole, benzothiazole, benzoxazole, thiadiazole, oxazole,.pyrrole, imidazole, and isoxazole.

The term "heterocyclic ring" refers to any 3-, 4-, 5-, 6-, or 7-membered nonaromatic ring containing at least one nitrogen atom which is bonded to an atom which is not part of the heterocyclic ring. In addition, the heterocyclic ring may also contain a one additional heteroatom which may be nitrogen, oxygen, or sulfur.

Compounds of the invention which have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope.

As mentioned above, the medical device or instrument may be made, such that at least in those portions of it which come into contact with blood, blood components or products, or vascular tissue, include a nitric oxide adduct. The nitric oxide adduct can directly or indirectly be linked to a synthetic material from which all or a portion of the device is formed. As representative examples, there may be mentioned: nylon, polyethylene perthalate (Dacron), polytetrafluoroethylene (Gortex).

In another embodiment mentioned above, the nitric oxide adduct can be incorporated into a natural or synthetic matrix which is then used to coat those same contact surfaces of the device. The matrix can be a liquid into which the nitric oxide adduct has been mixed, which is then coated onto the contact surfaces of the medical device or instrument and then allowed to "set", dry, polymerize or otherwise become solid or semisolid. Examples of such matrix materials include gel-forming materials such as are commonly used including hydrogels and starch-based semi-solid emulsions and dispersions.

The materials can also be polymers or mixtures of polymers such as polylactic acid/polylysine copolymer. Alternatively, the matrix can be a natural or synthetic fibrous matrix which is impregnated with a liquid containing the nitric oxide adducts either before or after being applied to the artificial contact surface. Examples of such natural fibrous matrix materials primarily include filter paper. Examples of such synthetic fibrous matrix materials include three-dimensional lattices of synthetic polymers and copolymers.

The matrix can also be a material such as nylon or plastic, such as polystyrene, that is directly or indirectly, i.e., through a linking group, derivitized with the nitric oxide adduct.

As mentioned above the nitric oxide adduct is specifically intended to be delivered locally at the site of contact of the device or instrument with the blood, blood product or component, or vasculature, but need not be physically associated with the device or instrument. For example, the nitric oxide adduct can be separately administered in a physiologically available form as a pharmaceutical preparation in a pharmaceutically acceptable carrier, such as are described in more detail below. This can be done by administration during or shortly before the contact or intervention. Where the device is, for example, a catheter, such as a cardiac catheter, the nitric oxide adduct preparation can be administered by injection into the lumen of the catheter.

Compounds contemplated for use in the invention are nitric oxide and compounds that release nitric oxide or otherwise directly or indirectly deliver or transfer nitric oxide to a site of its activity, such as on a cell membrane, in vivo. As used here, the term "nitric oxide" encompasses uncharged nitric oxide(NO•) and charged nitric oxide species, particularly including nitrosonium ion($NO^-$) and nitroxyl ion($NO^-$). The reactive form of nitric oxide can be provided by gaseous nitric oxide. The nitric oxide releasing, delivering or transferring compounds, having the structure X-NO wherein X is a nitric oxide releasing, delivering or transferring moiety, include any and all such compounds which provide nitric oxide to its intended site of action in a form active for their intended purpose. As used here, the term "nitric oxide adducts" encompasses any of such nitric oxide releasing, delivering or transferring compounds, including, for example, S-nitrosothiols, S-nitroso amino acids, S-nitroso-polypeptides, and nitrosoamines. It is contemplated that any or all of these "nitric oxide adducts" can be mono- or poly- nitrosylated at a variety of naturally susceptible or artificially provided binding sites for nitric oxide.

One group of such nitric oxide adducts is the S-nitrosothiols, which are compounds that include at least one —S—NO group. Such compounds include S-nitroso-polypeptides (the term "polypeptide" includes proteins and also polyamino acids that do not possess an ascertained biological function, and derivatives thereof); S-nitrosylated amino acids(including natural and synthetic amino acids and their stereoisomers and racemic mixtures and derivatives thereof); S-nitrosated sugars, S-nitrosated-modified and unmodified oligonucleotides (preferably of at least 5, and more particularly 5–200, nucleotides); and an S-nitrosated hydrocarbon where the hydrocarbon can be a branched or unbranched, and saturated or unsaturated aliphatic hydrocarbon, or an aromatic hydrocarbon; S-nitroso hydrocarbons having one or more substituent groups in addition to the S-nitroso group; and heterocyclic compounds. S-nitrosothiols and the methods for preparing them are described in U.S. patent application Ser. No. 07/943,834, filed Sep. 14, 1992, Oae et al., *Org. Prep. Proc. Int.*, 15(3):165–198, 1963; Loscalzo et al., *J. Pharmacol. Exp. Ther.*, 249(3):726729, 1989, and Kowaluk et al., *J. Pharmacol. Exp. Ther.*, 256:1256–1264, 1990, all of which are incorporated in their entirety by reference.

One particularly preferred embodiment of this aspect relates to S-nitroso amino acids where the nitroso group is linked to a sulfur group of a sulfur-containing amino acid or derivative thereof. For example, such compounds include the following: S-nitroso-N-acetylcysteine, S-nitroso-captopril, S-nitroso-homocysteine, S-nitroso-cysteine and S-nitroso-glutathione.

Suitable S-nitrosylated proteins include thiol-containing proteins(where the NO group is attached to one or more sulfur group on an amino acid or amino acid derivative thereof) from various functional classes including enzymes, such as tissue-type plasminogen activator(TPA) and cathepsin B; transport proteins, such as lipoproteins, heme proteins such as hemoglobin and serum albumin; and biologically protective proteins, such as the immunoglobulins and the cytokines. Such nitrosylated proteins are described in PCT Publ. Applic. No. WO 93/09806, published May 27, 1993. Examples include polynitrosylated albumin where multiple thiol or other nucleophilic centers in the protein are modified.

Further examples of suitable S-nitrosothiols include those having the structures:

 (i)

wherein x equals 2 to 20;

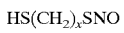 (ii)

wherein x equals 2 to 20; and

 (iii)

wherein x equals 2 to 20 and Y is selected from the group consisting of halo, alkoxy, cyano, carboxamido, cycloalkyl, arylalkoxy, lower alkylsulfinyl, arylthio, alkylamino, dialkylamino, hydroxy, carbamoyl, N-alkylcarbamoyl, N,N-dialkylcarbamoyl, amino, hydroxyl, carboxyl, hydrogen, nitro and aryl.

Other suitable S-nitrosothiols that are S-nitroso-angiotensin converting enzyme inhibitors (hereinafter referred to as S-nitroso-ACE inhibitors) are described in Loscalzo, U.S. Pat. No. 5,002,964 (1991) and Loscalzo et al., U.S. Pat. No. 5,025,001 (1991) both of which are incorporated in their entirety by reference. Examples of such S-nitroso-ACE inhibitors include compounds having structure (1):

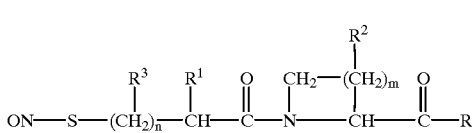

1 wherein

R is hydroxy, $NH_2$, $NHR^4$, $NR^4R^5$, or lower alkoxy, wherein $R^4$ and $R^5$ are lower alkyl, or aryl, or arylalkyl;

$R^1$ is hydrogen, lower alkyl, arylalkyl, amino, guanidino, $NHR^6$, $NlR^6R^7$, wherein $R^6$ and $R^7$ are methyl or alkanoyl;

$R^2$ is hydrogen, hydroxy, $C_1$–$C_4$ alkoxy, phenoxy, or lower alkyl;

$R^3$ is hydrogen, lower alkyl or arylalkyl;

m is 1 to 3; and n is 0 to 2.

Other suitable S-nitroso-ACE inhibitors include N-acetyl-S-nitroso-D-cysteinyl-L-proline, N-acetyl-S-nitroso-D,L-cysteinyl-L-proline, 1-[4-amino-2-(S-nitroso) mercaptomethyl butanoyl]-L-proline, 1-[2-hexanoyl]-L-proline, 1-[5-guanidino-2-(S-nitroso)mercaptomethyl-pentanoyl]-L-proline, 1-[5-amino-2-(S-nitroso) mercaptomethyl-pentanoyl]-4-hydroxy-L-proline, 1-[5-guanidino-2-(S-nitroso)mercaptomethyl-pentanoyl]-4-hydroxy-L-proline, 1-[2-aminomethyl-3(S-nitroso)-mercaptomethyl-pentanoyl-L-proline, and S-nitroso-L-cysteinyl-L-proline.

Additional suitable S-nitroso-ACE inhibitors include those having structures (2–3):

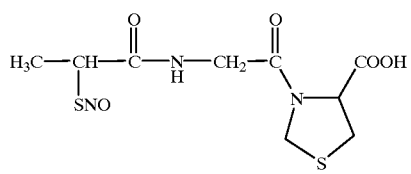

2

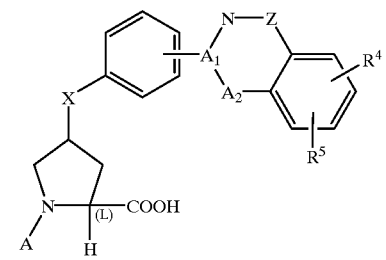

3 wherein

X is oxygen or sulfur;

—A₁, —A₂— is CH—NH or —C=N—;

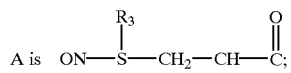

R is selected from hydrogen, lower alkyl, arylalkyl, and salt forming ion;

R₄ and R₅ are independently selected from hydrogen, halogen, lower alkyl, lower alkoxy, halo substituted lower alkyl, nitro, and SO₂NH₂;

Z is

or

R₆ is hydrogen, lower alkyl, halo substituted lower alkyl, hydroxy substituted lower alkyl, —(CH₂)$_q$—N (lower alkyl)₂ or —(CH₂)$_q$—NH₂ and q is one, two, three or four; and

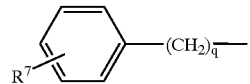

wherein R⁷ is hydrogen, lower alkyl, alkoxy, halogen or hydroxy and g is as defined above.

Additional suitable compounds include those having structures (4–11):

(4)
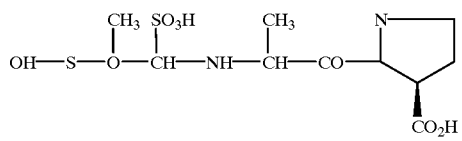

(5)
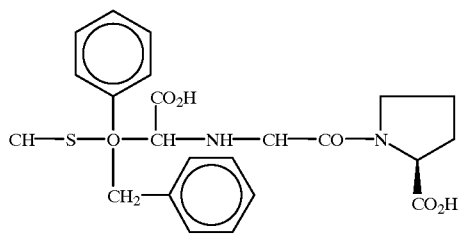

-continued (6)
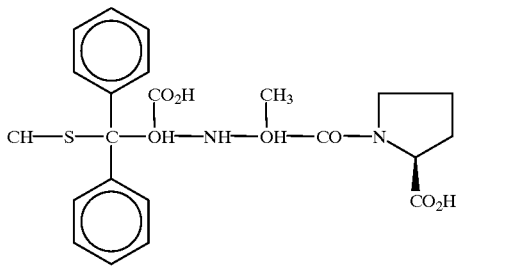

(7)
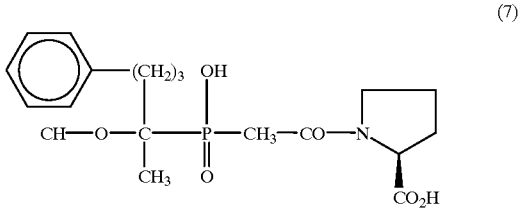

(8)
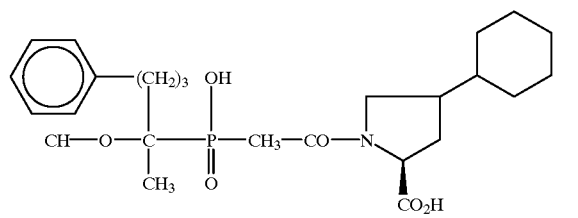

(9)
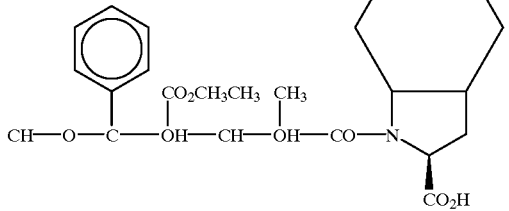

(10)
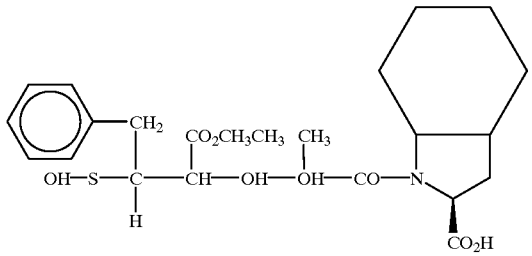

(11)
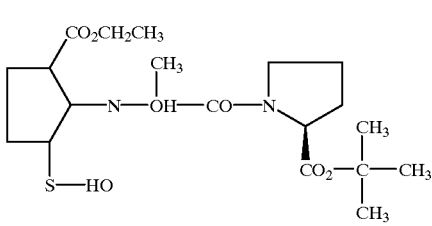

The S-nitroso-ACE inhibitors can be prepared by various methods of synthesis. In general, the thiol precursor is prepared first, then converted to the S-nitrosothiol derivative by nitrosation of the thiol group with $NaNO_2$ under acidic conditions (pH=1 to 5) which yields the S-nitroso derivative. Acids which may be used for this purpose include aqueous sulfuric, acetic and hydrochloric acids. Thiol precursors are prepared as described in the following: U.S. Pat. No. 4,046,889 (1977); U.S. Pat. Nos. 4,052,511; 4,053,651; 4,113,751, 4,154,840, 4,129,571 (1978), and U.S. Pat. No. 4,154,960 (1979) to Ondetti et al.; U.S. Pat. No. 4,626,545 (1986) to Taub; and U.S. Pat. No. 4,692,458 (1987) and U.S. Pat. No. 4,692,459 (1987) to Ryan et al., Quadro, U.S. Pat. No. 4,447,419 (1984); Haugwitz et al.; U.S. Pat. No. 4,681,886 (1987), Bush et al., U.S. Pat. No. 4,568,675 (1986), Bennion et al., U.S. Pat. No. 4,748,160 (1988), Portlock, U.S. Pat. No. 4,461,896 (1984), Hoefle et al., European Patent Application Publication No. 0 088 341 (1983), Huange et al., U.S. Pat. No. 4,585,758 (1986), European Patent application Publication No. 0 237 239, European Patent application Publication No. 0 174 162, published in 1986, European Patent application Publication No. 0 257 485, published in 1988, all of which are incorporated by reference herein.

Another group of such NO adducts are compounds that include at least one —O—NO group. Such compounds include O-nitroso-polypeptides(the term "polypeptide" includes proteins and also polyamino acids that do not possess an ascertained biological function, and derivatives thereof); O-nitrosylated amino acids (including natural and synthetic amino acids and their stereoisomers and racemic mixtures and derivatives thereof); O-nitrosated sugars; O-nitrosated-modified and unmodified oligonucleotides (preferably of at least 5, and more particularly 5–200, nucleotides); and an O-nitrosated hydrocarbon where the hydrocarbon can be a branched or unbranched, saturated or unsaturated aliphatic hydrocarbon, or an aromatic hydrocarbon; O-nitroso hydrocarbons having one or more substituent groups in addition to the O-nitroso group; and heterocyclic compounds.

Another group of such NO adducts is the nitrites which have an —O—NO group wherein R is a protein, polypeptide, amino acid, branched or unbranched and saturated or unsaturated alkyl, aryl or a heterocyclic. A preferred example is the nitosylated form of isosorbide. Compounds in this group form S-nitrosothiol intermediates in vivo in the recipient human or other animal to be treated and can therefore include any structurally analogous precursor R—O—NO of the S-nitrosothiols described above.

Another group of such NO adducts is the N-nitrosoamines, which are compounds that include at least one —N—NO group. Such compounds include N-nitroso-polypeptides (the term "polypeptide" includes proteins and also polyamino acids that do not possess an ascertained biological function, and derivatives thereof); N-nitrosylated amino acids (including natural and synthetic amino acids and their stereoisomers and racemic mixtures); N-nitrosated sugars; N-nitrosated-modified and unmodified oligonucleotides (preferably of at least 5, and more particularly 5–200, nucleotides); and an N-nitrosated hydrocarbon where the hydrocarbon can be a branched or unbranched, and saturated or unsaturated aliphatic hydrocarbon, or an aromatic hydrocarbon; N-nitroso hydrocarbons having one or more substituent groups in addition to the N-nitroso group; and heterocyclic compounds.

Another group of such NO adducts is the C-nitroso compounds that include at least one —C—NO group. Such compounds include C-nitroso-polypeptides (the term "polypeptide" includes proteins and also polyamino acids that do not possess an ascertained biological function, and derivatives thereof); C-nitrosylated amino acids (including natural and synthetic amino acids and their stereoisomers and racemic mixtures); C-nitrosated sugars; C-nitrosated-modified and unmodified oligonucleotides (preferably of at least 5, and more particularly 5–200, nucleotides); and a C-nitrosated hydrocarbon where the hydrocarbon can be a branched or unbranched, and saturated or unsaturated aliphatic hydrocarbon, or an aromatic hydrocarbon; C-nitroso hydrocarbons having one or more substituent groups in addition to the C-nitroso group; and heterocyclic compounds.

Another group of such NO adducts is the nitrates which have at least one —O—$NO_2$ group. Such compounds include polypeptides (the term "polypeptide" includes proteins and also polyamino acids that do not possess an ascertained biological function, and derivatives thereof); amino acids (including natural and synthetic amino acids and their stereoisomers and racemic mixtures and derivatives thereof); sugars; modified and unmodified oligonucleotides (preferably of at least 5, and more particularly 5–200, nucleotides); and a hydrocarbon where the hydrocarbon can be a branched or unbranched, and saturated or unsaturated aliphatic hydrocarbon, or an aromatic hydrocarbon; hydrocarbons having one or more substituent groups; and heterocyclic compounds. A preferred example is nitroglycerin.

Another group of such NO adducts is the nitroso-metal compounds which have the structure $(R)_n$—A—M—$(NO)_x$. R includes polypeptides(the term "polypeptide" includes proteins and also polyamino acids that do not possess an ascertained biological function, and derivatives thereof); amino acids (including natural and synthetic amino acids and their stereoisomers and racemic mixtures and derivatives thereof); sugars; modified and unmodified oligonucleotides (preferably of at least 5, and more particularly 5–200, nucleotides); and a hydrocarbon where the hydrocarbon can be a branched or unbranched, and saturated or unsaturated aliphatic hydrocarbon, or an aromatic hydrocarbon; hydrocarbons having one or more substituent groups in addition to the A-nitroso group; and heterocyclic compounds. A is S, O, or N, n and x are each integers independently selected from 1, 2 and 3, and M is a metal, preferably a transition metal. Preferred metals include iron, copper, manganese, cobalt, selenium and luthidium. Also contemplated are N-nitrosylated metal centers such as nitroprusside.

Another group of such NO adducts is the N-oxo-N-nitrosoamines which have an R—N($O^-M^+$)—NO group or an R—NO—NO-group. R includes polypeptides (the term "polypeptide" includes proteins and also polyamino acids that do not possess an ascertained biological function, and derivatives thereof); amino acids(including natural and synthetic amino acids and their stereoisomers and racemic mixtures and derivatives thereof); sugars; modified and unmodified oligonucleotides (preferably of at least 5, and more particularly 5–200, nucleotides); and a hydrocarbon where the hydrocarbon can be a branched or unbranched, and saturated or unsaturated aliphatic hydrocarbon, or an aromatic hydrocarbon; hydrocarbons having one or more substituent groups; and heterocyclic compounds. R is preferably a nucleophilic (basic) moiety. M+ is a metal cation, such as, for example, a Group I metal cation.

Another group of such NO adducts is the thionitrates which have the structure R—$(S)_x$—NO wherein x is an integer of at least 2. R is as described above for the S-nitrosothiols. Preferred are the dithiols wherein x is 2. Particularly preferred are those compounds where R is a polypeptide or hydrocarbon and a pair or pairs of thiols are sufficiently structurally proximate, i.e. vicinal, that the pair of thiols will be reduced to a disulfide. Those compounds which form disulfide species release nitroxyl ion($NO^-$) and uncharged nitric oxide($NO\bullet$). Those compounds where the thiol groups are not sufficiently close to form disulfide bridges generally only provide nitric oxide as the $NO^-$ form not as the uncharged $NO\bullet$ form.

Coating of a surface of a medical device with the nitric oxide adduct comprises contacting the surface with the adduct so as to cause the surface to be coated with the particular adduct. Coating of the artificial surface may be accomplished using the methods described in Example 1, infra, or other standard methods well known to those of ordinary skill in the art. For example, coating a surface with nitric oxide adducts can be achieved by bathing the artificial surface, either by itself or within a device, in a solution containing the nitric oxide adduct. In addition, synthetic nitric oxide adducts may be coated onto an artificial surface by a variety of chemical techniques which are well known in the art. Such techniques include attaching the adduct to a nucleophilic center, metal, epoxide, lactone, an alpha- or beta-saturated carbon chain, alkyl halide, carbonyl group, or Schiff base, by way of the free thiol.

In order to optimize the coating techniques further, standard methods may be used to determine the amount of platelet deposition on a sample of the treated artificial surface. Such methods include the--use of $^{51}Cr$-labeled platelets or $Indium^{111}$-labeled platelets. Other well known techniques for evaluating platelet deposition on artificial surfaces are described in Forbes et al. (1978), and Salzman et al. (1981).

It is also contemplated that artificial surfaces will vary depending on the nature of the surface, and such characteristics as contour, crystallinity, hydrophobicity, hydrophilicity, capacity for hydrogen bonding, and flexibility of the molecular backbone and polymers. Therefore, using routine methods, one of ordinary skill will be able to customize the coating technique by adjusting such parameters as the amount of adduct, length of treatment, temperature, diluents, and storage conditions, in order to provide optimal coating of each particular type of surface.

After the device or artificial material has been coated with the nitric oxide adduct, it will be suitable for its intended use, for example, implantation as a heart valve, insertion as a catheter, or for cardiopulmonary oxygenation or hemodialysis. The coated device or artificial surface will be suitable for use in conjunction with an animal, preferably mammals, including humans.

Another embodiment of a nitric oxide adduct pertains to the derivatization of synthetically derived polymeric materials. Nitric oxide adducts of the formula IA wherein b is an integer from 270 to 500, c is an interger of 1 to 2, d is an integer from 1 to 6, E is a covalent bond, S, N, O, or C—N—C(O)—$R^0$, in which $R^0$ is H. lower alkyl, cycloalkyl, aryl, heteroaryl, or heterocyclic ring system may be prepared according to the reaction scheme depicted in FIG. 7A, in which the biodegradable poly L-lactic acid/poly-L-lysine copolymer prepared as described by Berrera et al., J. Am. Chem. Soc., 115:11010, 1993) is representative of the synthetic polymeric materials defined above. The primary amino groups of the compound of formula 13 are reacted with a compound of formula 14, wherein T is an activated carbonyl-containing substituent selected from a group consisting of a mixed anyhdride, a thioester, an acid chloride, an isocyanate, or a chloroformate, $P^1$ is a sulfur protecting group, and E and d are defined as above to afford a compound of the formula 15 wherein b, c, E, d, and $P^1$ are defined as above. A variety of sulfur protecting groups which are compatible with this process along with methods for their incorporation and removal are described in T. H. Greene and P. G. M. Wuts, *Protective Groups in Organic Synthesis*, 2nd edition, John Wiley & Sons, New York, 1991. The sulfur protecting groups in the compound of the formula 15 are removed to afford the compound of the formula 16 and the thiol moieties are nitrosated to afford a compound of the formula IA using a suitable mild nitrosating agent such as nitrosyl chloride or nitrosonium tetrafluoroborate in an inert organic solvent or mixture of inert solvents such as methylene chloride, chloroform, dimethyforamide (DMF), dimethylsulfoxide (DMSO), ethyl acetate, or acetonitrile. In addition, the nitrosation may be performed in the presence or absence of an amine base such as pyridine or triethylamine. Alternatively, the nitrosation of the compound of the formula 16 may be performed with nitrous acid generated in situ from sodium nitrite and hydrochloric acid in an aqueous or mixed aqueous and organic solvent system to afford a compound of the formula IA.

Figure 1B:
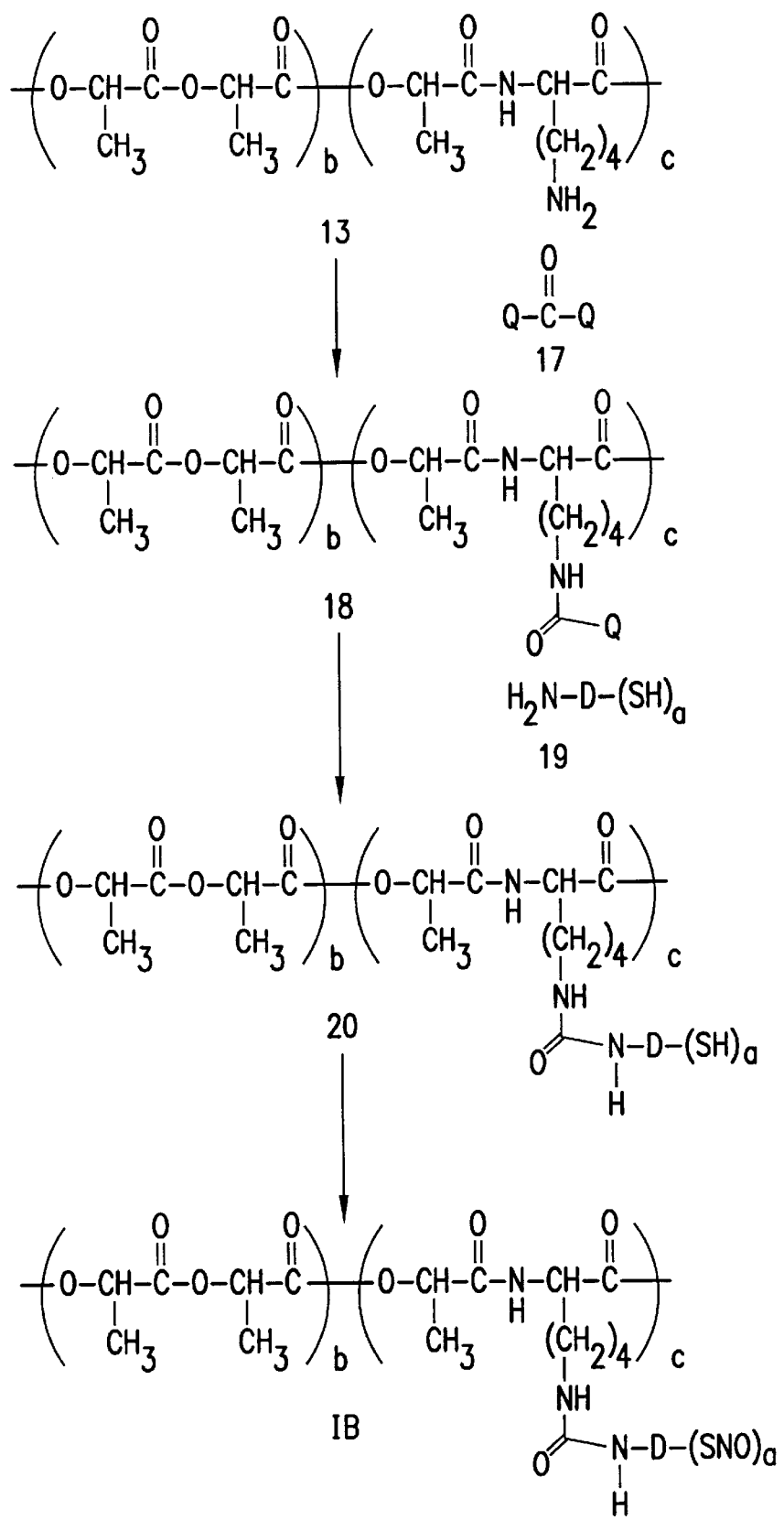
FIG. 1B is a synthetic scheme for the preparation of a nitrosothiol incorporated on to the $\epsilon$-amino group of a copolymer comprised of poly-L-lactic acid-co-L-lysine.

Nitric oxide adducts of the formula 1B wherein b is an integer from 270 to 500, c is an integer of 1 to 2, D is a thiol containing amino acid or peptide of 1 to 10 amino acids containing 1 to 10 thiols or a thiol containing carboxylic acid containing 1 to 10 thiol groups, a is an integer from 1 to 10, and b and c are defined as above may be prepared according to the reaction scheme depicted in FIG. 1B, in which the biodegradable poly L-lactic acid/poly-L-lysine copolymer prepared as described by Berrera et al. is representative of the synthetic polymeric materials defined above. The primary amino groups of the compound of the formula 13 wherein b and c are defined as above may be acylated with a compound of the formula 17 wherein Q is halogen, imidazolyl, or trihalomethoxy in a suitable inert solvent or mixture of solvents such as DMSO and methylene chloride to afford a compound of the formula 18. The compound of the formula 18 is then reacted with a compound of the formula 19 wherein D and a are as defined above to afford a compound of the formula 20. The compound of the formula 20 is then nitrosated to afford a compound of the formula 1B with a suitable mild nitrosating agent such as nitrosyl chloride or nitrosonium tetrafluoroborate in an inert organic solvent or mixture of inert solvents such as methylene chloride, chloroform, dimethyforamide (DMF), dimethylsulfoxide (DMSO), ethyl acetate, or acetonitrile. In addition, the nitrosation may be performed in the presence or absence of an amine base such as pyridine or triethylamine. Alternatively, the nitrosation of the compound of the formula 20 may be performed with nitrous acid generated in situ from sodium nitrite and hydrochloric acid in an aqueous or mixed aqueous and organic solvent system to afford a compound of the formula 1B.

Another example of a nitric oxide adduct derived from a synthetic polymeric material is the modification of the L-cysteine amino acid residues immobilized to modified surface of poly(ethyleneterephalate) which has been activated by pretreatment with 3-aminopropyltriethoxysilane followed by glutaraldehyde as described by Bui et al., *The Analyst*, 118:463 (1993). The cysteine thiols may be nitrosated with a suitable nitrosating agent such as nitrous acid generated in situ from sodium nitrite and hydrochloric acid in an aqueous or mixed aqueous and organic solvent system or, alternatively, with nitric oxide gas or nitrosyl chloride in a suitable inert solvent to afford the polymer containing the nitric oxide adduct.

Figure 2:
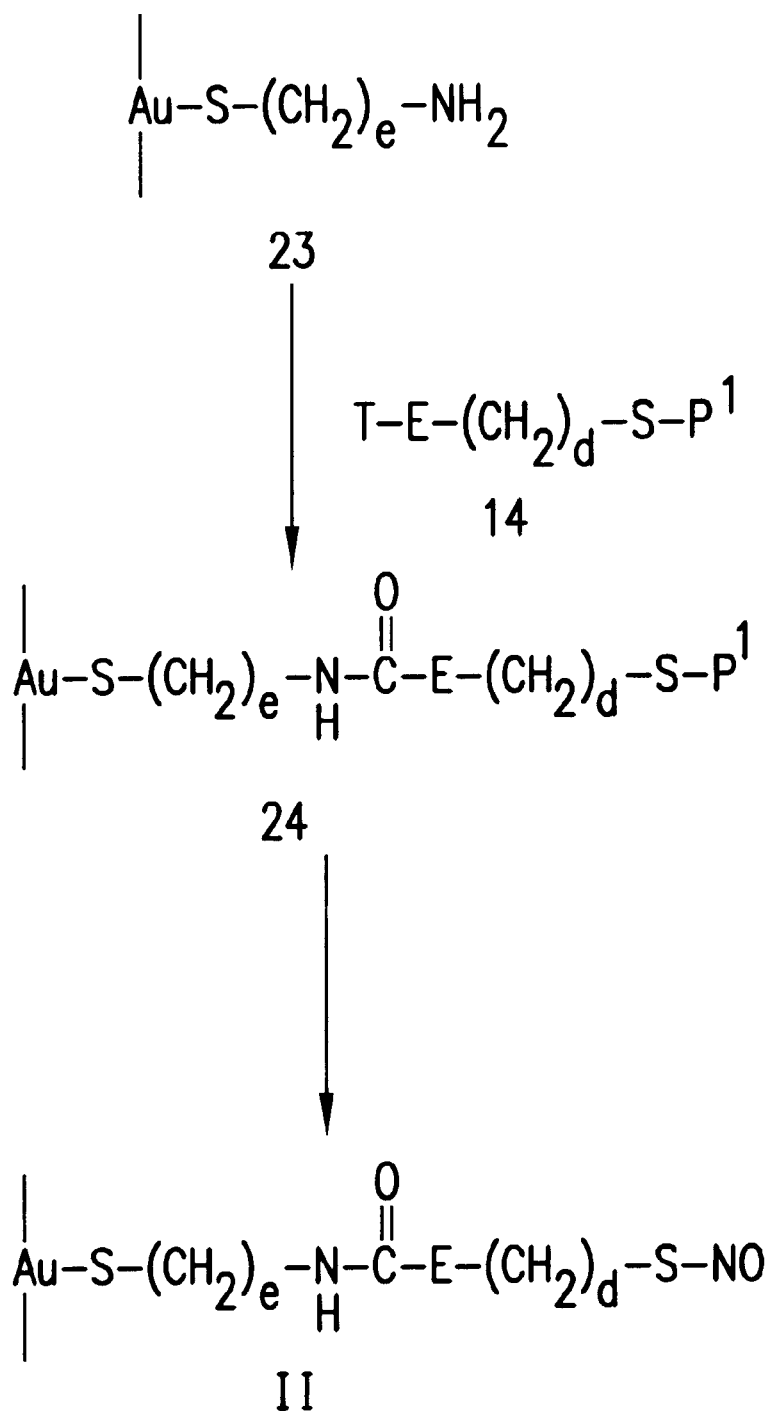
FIG. 2 is a synthetic scheme for the preparation of a nitrosothiol incorporated on to an amino derivatized self-assembled monolayer (SAMS) adsorbed to a gold surface.

Yet another embodiment of a nitric oxide adduct pertains to the derivatization of a gold or gold coated surface with a self-assembled monolayer (SAMS) of an ω-substituted alkanethiolate or mixture of ω-substituted alkanethiolates or ω-substituted alkanethiolates and unsubstituted alkanethiolates. Functionalized surfaces of SAMS terminating in carboxylic acids [Collison et al. *Langmuir,* 8:1247, 1992,; Leggett et al., *Langmuir,* 9:2356, 1993] or amines [whitesell et al., *Angew. Chem. Int. Ed. Engl.,* 33:871, 1994] have previously been prepared. These functionalized SAMS may be further derivatized with organic groups containing one or more nitric oxide adducts as depicted in FIG. 2.

For another example, the amine groups of the SAMS surface composed of the compound of the formula 23 wherein e is an interger from 2 to 20 may be reacted with a compound of the formula 14 wherein T, E, d and $P^1$ are defined as above to afford a SAMS surface composed of a compound of the formula 24. After deprotection of the thiol moieties of the compound of the formula 24, the free thiol groups are nitrosated to afford a compound of the formula IIB using a suitable mild nitrosating agent such as nitrosyl chloride or nitrosonium tetrafluoroborate in an inert organic solvent or mixture of inert solvents such as methylene choloride, chloroform, dimethyformamide (DMF), dimethylsulfoxide (DMSO), ethyl acetate, or acetonitrile. In addition, the nitrosation may be performed in the presence or absence of an amine base such as pyridine or triethylamine. Alternatively, the nitrosation of the free thiol groups may be performed with nitrous acid generated in situ from sodium nitrite and hydrochloric acid in an aqueous or mixed aqueous and organic solvent system to afford a compound of the formula II.

Particularly preferred nitric oxide adducts are polynitrosylated peptides and proteins. Synthesis of polynitrosated peptides and proteins can be achieved in several ways. 1) Mono S-nitrosylation is best achieved by incubating peptides and proteins (in deionized water in an equimolar concentration of acidified nitrite (final concentration 0.5 N HCl) for a period of 1–30 minutes. The incubation time depends on the efficiency of nitrosation and the tolerance of the protein. Nitrosation can also be achieved with a variety of other nitrosating agents including compounds such as S-nitroso-cystein, S-nitroso-glutathione and related alkyl nitrites. These compounds are to be used when the peptide or protein does not tolerate harsh acidic conditions, e.g. human hemoglobin.

There are two principal ways of achieving poly S-nitrosation. In the first, the peptide or protein is reduced in 100–1000 molar excess dithiothreitol for 30–60 minutes. This exposes intramolecular thiols. The peptide or protein is separated from dithiothreitol by gel filtration (G-25). The protein is then exposed to increasing concentrations of acidified nitrite (0.5 N HCl) in relative excess over protein. Complementary measurements of Saville indicate when S-nitrosation is complete. For example, with albumin, this procedure leads to approximately 20 intramolecular S—NO derivatives.

Alternatively, the protein can be treated with thiolating agent such as homocysteine thiolactone. This tends to add homocystine groups to exposed amine residues in proteins. The derivatized protein can then be S-nitrosated by exposure to acidified nitrite. Exposure to incerasing concentrations of nitrite with complementary measurements of Saville can be used to ascertain when S-nitrosation is maximal. Alternatively, thiol groups can be quantified on the protein using standard methodologies and then the protein treated with a stoichiometric concentration of acidified nitrite (0.5 N HCl).

Polynitrosation of nucleophilic functional groups (other than thiol) can be achieved when proteins are incubated with excess acidified nitrite. The order of protein reactivity is tyrosine followed by amines on residues such as trytophan. Amide linkages are probably less reactive. Accordingly, many NO groups can be added to proteins by simply incubating the protein with high excess acidified nitrite. For example, exposure of albumin to 1000 fold excess nitrite leads to approximately 200 moles of NO/mole protein. These experiments are performed in 0.5 normal HCl with incubations for approximately one hour. $^{15}N$ NMR can be used to determine where the addition (or substitution) by NO takes place.

Finally, nitrosation can be achieved by exposure to authentic nitric oxide gas under anaerobic conditions. For successful nitrosation proteins should be incubated in at least 5 atmospheres of No gas for several hours. Incubation time is protein specific. This can lead to NO attachment to a variety of protein bases. Best characterized reactions involve primary amines. This mechanism provides a pathway to sustain N-nitrosation reactions without deamination. Specifically, exposure to acidified nitrite would otherwise lead to deamination of primary amines whereas this method leads to formation of N-hydroxynitrosamines with potent bioactivity. Similar substitutions at other basic centers also occur.

The method of the invention provides significant advantages over current attempts to reduce platelet deposition on artificial surfaces. As demonstrated by the inventors, a surface can be coated with nitric oxide adducts using simple, effective methods. The coated surfaces may be used immediately, or stored and used at a later date. In addition, by coating the surface itself, this method eliminates the need for systemic administration of anti-thrombogenic agents which are often ineffective, have serious adverse side effects, or are unsuitable for use in certain patients. Also, the inhibition of platelet deposition provided by the invention is completely and immediately reversible, a need which is especially important in patients with cardiac or vascular disease.

By preventing platelet deposition or thrombus formation, the invention is also useful in preventing serious vascular complications associated with the use of medical devices. These complications occur as a result of increased platelet deposition, activation, and thrombus formation or consumption of platelets and coagulation proteins. Such complications are well known to those of ordinary skill in the medical arts and include myocardial infarction, pulmonary thromboembolism, cerebral thromboembolism, thrombophlebitis, thrombocytopenia, bleeding disorders and any additional complication which occurs either directly or indirectly as a result of the foregoing disorders.

In another embodiment, the invention relates to a method for preventing the deposition of platelets on a surface comprising contacting the surface with a nitric oxide adduct in combination with at least one additional anti-thrombogenic agent. The term "anti-thrombogenic" agent refers to any compound which alters platelet function, or interferes with other mechanisms involved in blood clotting, such as fibrin formation. Examples of such compounds include, but are not limited to, heparin, warfarin, aspirin, indomethacin, dipyridamole prostacyclin, prostaglandin-$E_1$ or sulfinpyrazone.

This method for coating a surface with a nitric oxide adduct in combination with another anti-thrombogenic agent will be accomplished using the methods described previously for coating a surface with a nitric oxide adduct alone, and are suitable for any and all types of natural tissue and artificial surfaces. The appropriate coating concentration of the other anti-thrombogenic compound is determined using routine methods similar to those described previously. The coated surfaces may be used in the same manner described for those surfaces coated with nitric oxide adducts alone.

By coating a surface with a nitric oxide adduct in combination with at least one other anti-thrombogenic agent, one will be able to not only prevent platelet deposition, which is the initial event in thrombus formation, but also to limit fibrin formation directly, by inhibiting factor VIII, and platelet granule secretion, and indirectly, by inhibiting plasminogen activator inhibitor (PAI-1) release from platelets. Thus, by coating a surface with agents that both prevent platelet deposition and interfere with other platelet functions which contribute to coagulation, the invention provides a further means for preventing thrombus formation.

In a further embodiment, the invention relates to a method for preventing thrombus formation on a damaged vascular surface in an animal, comprising applying a nitric oxide adduct directly to the damaged surface. The term "damaged vascular surface" refers to any portion of the interior surface of a blood vessel in which damage to the endothelium or subendothelium, narrowing or stenosis of the vessel has occurred. The invention is especially suitable for use in coronary arteries, but is beneficial in other damaged arteries and also in veins including particularly those used in arterial or venous bypass replacement where they are susceptible to damage from the typically higher arterial pressures to which they are unaccustomed.

The nitric oxide adduct is applied directly to the damaged vascular surface by using an intraarterial or intravenous catheter, suitable for delivery of the adduct to the desired location. The location of damaged arterial surfaces is determined by conventional diagnostic methods, such as X-ray angiography, performed using routine and well-known methods available to those of skill within the medical arts. In addition, administration of the nitric oxide adduct using an intraarterial or intravenous catheter is performed using routine methods well known to those in the art. Typically, the preparation is delivered to the site of angioplasty through the same catheter used for the primary procedure, usually introduced to the carotid or coronary artery at the time of angioplasty balloon inflation.

The compounds of this invention can be employed in combination with conventional excipients, i. e., pharmaceutically acceptable organic or inorganic carrier substances suitable for parenteral application which do not deleteriously react with the active compounds. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions preferably oily or aqueous solutions, as well as suspensions, emulsions, or implants. Aqueous suspensions may contain substances which increase the viscosity of the suspension and include, for example, sodium carboxymethyl cellulose, sorbitol, and/ or dextran. Optionally, the suspension may also contain stabilizers.

The term "therapeutically effective amount," for the purposes of the invention, refers to the amount of the nitric oxide adduct which is effective to achieve its intended purpose. While individual needs vary, determination of optimal ranges for effective amounts of each nitric oxide adduct is within the skill of the art. Generally, the dosage required to provide an effective amount of the composition, and which can be adjusted by one of ordinary skill in the art will vary, depending on the age, health physical condition, sex, weight, extent of disease of the recipient, frequency of treatment and the nature and scope of the desired effect. The preparations, which are suitable for treatment of artificial surfaces, such as of a medical device, and endothelium are used in concentrations of about 500–700 mM of adduct delivered by drip infusion sterile in a physiological liquid over 2–3 minute periods in amounts of 2–3 ml per 25 kg body weight.

As demonstrated by the inventors, direct application of a nitric oxide adduct to a damaged vascular surface, coats the surface, thereby decreasing the thrombogenicity of the surface. As further demonstrated by the inventors, local application of the nitric oxide adduct to the damaged vascular surface can be accomplished at doses much lower than those required to exert a systemic effect. Thus, this method provides a significant and an unexpected advantage over the use of systemic anti-thrombogenic agents to prevent thrombus formation in damaged vessels.

EXAMPLE 1

NO Adducts Make Artificial Surfaces Less Thrombogenic

One of the best ways to demonstrate that an artificial surface exposed to blood has been made less thrombogenic is to measure or quantitate the number of blood platelets that collect on that surface. This method requires the removal of platelets from an animal or human subject. The platelets are labeled with a radioactive material such as Indium$^{111}$, which emits gamma rays, detectable by a gamma counter placed 3 to 6 inches away from the source of radioactive platelets. The labeled platelets are either reinjected into the animal or human in vivo, or contacted with the artificial surface in vivo. Platelets will adhere to artificial surfaces or acutely damaged arterial surfaces. Thus, the number of normal platelets and radioactive platelets which stick to the surface is an indication of the thrombogenicity of the surface.

The inventors have used this methodology in experiments to demonstrate that nitric oxide adducts decrease the thrombogenicity of an artificial surface or a damaged natural arterial surface. The following experiments demonstrate that coating artificial surfaces, such as synthetic vascular graft material, with a nitric oxide adduct, decreases platelet deposition and makes the surface significantly less thrombogenic than previously used agents such as albumin alone. In addition, the experiments demonstrate that polyvinyl chloride (PVC) tubing, which is used extensively in artificial kidney and heart-lung machines, can be coated with an nitric oxide adduct such as S-nitroso-albumin, to make it less thrombogenic.

Protection of Synthetic Vascular Grafts

First, the inventors coated dacron grafts and cardiac catheters with S-nitroso-bovine serum albumin (BSA). In three separate experiments, an identical pair of 6 mm. (internal diameter) knitted dacron grafts, 5 cm. in length, were prepared for surgical placement in the transected carotid arteries of three anesthetized dogs. No heparin was given. One graft was soaked in 5% BSA and the other graft was soaked in 5% BSA combined with 0.5 mM nitric oxide (producing S-nitroso-BSA) for one hour prior to insertion, and then rinsed in saline. The grafts were sutured in place with a continuous 6-0 proline suture.

Indium-labeled platelets

Indium[111]-labeled platelets are very useful in detecting platelet accumulation on vascular grafts. Therefore, Indium[111]-labeled platelets were prepared according to standard methods described in Heyns "Method for Labeling Platelets with In[111]-oxine". In: *Platelet Kinetics and Imaging* Vol. II, Editors Heyns et al., CRC Press, 1985; and Sheffel et al., J. Nucl. Med., 20: 524–531, 1979, and injected prior to insertion of the grafts. Following graft insertion, the dogs were observed for two hours, then both grafts were removed, rinsed, and weighed. The grafts were then placed in a NaI gamma well counter and counted for four minutes.

The three grafts coated with BSA alone had an average of 654,000 +/−89,000 counts/4 minutes. In contrast, the three grafts coated with S-nitroso-BSA had an average of 278,000 +/57,000 counts/4 minutes (P<0.005). The average percent increase in weight for the three grafts due to thrombus formation on the luminal surface with BSA alone, was 410% +/−97%, while the percent increase in weight for the three grafts incubated with nitroso-BSA was 196% +/−71% (P<0.005).

These data show that during exposure of the graft to circulating blood over a period of two hours, there was considerably less platelet deposition and clotting on the synthetic grafts treated with S-nitroso-BSA. Thus the results demonstrate that S-nitroso-BSA coating of synthetic vascular grafts provides protection against early platelet deposition.

In addition, three pairs of 5 FR USC1 catheters were studied. One catheter was soaked in 5% BSA, while the other catheter was soaked in a mixture of S-nitroso BSA for one hour. The catheters were rinsed with saline and one each was inserted into the right or left femoral arteries of the dogs described above, and left for two hours. Each catheter was flushed with normal saline every one-half hour, but no heparin was given. The catheters were then removed and rinsed with saline. Equal lengths of the catheters were cut from the distal ends and each one was placed in a NaI gamma counter and the radioactivity was counted for four minutes.

The counts for the three catheters coated with BSA alone had an average count of 9,000±1,100. In contrast, the three catheters coated with 5% BSA+0.5 Mm nitric oxide had only 2,850±800 counts. Thus, there were significantly fewer platelets deposited on the catheters coated with S-nitroso-BSA, than those coated with BSA alone. These experiments demonstrate that synthetic vascular grafts coated with S-nitroso-BSA and immediately implanted, are significantly less thrombogenic than grafts coated with BSA alone.

The inventors conducted an additional experiment to investigate whether S-nitroso-BSA can be used to coat a surface such as polyvinyl chloride (PVC), and in addition, whether such surfaces can be treated at one time, and used at a later time. In this experiment, three pieces of PVC, 3 mm in internal diameter and 2 cm. in length were soaked in BSA for 4 hours, allowed to dry, and placed in a dark place. Three identical pieces of PVC tubing were soaked in an S-nitroso-BSA solution for 4 hours, dried, and also placed in the dark. The lengths of PVC tubing were kept in the dark to minimize potential inactivation of the nitric oxide-donating compounds caused by exposure to light.

Three days after coating, a pair of PVC tubing pieces, one coated with BSA, and one coated with S-nitroso-BSA, were placed as a shunt in each of the two femoral arteries of a dog. The dog was injected with Indium[111]-labeled platelets as previously described. Two hours after the PVC shunts were placed in the circulation with radioactive platelets, they were removed and placed in the NaI gamma counter.

The counts on the BSA coated shunt were 200,870/4 minutes, whereas on the S-nitroso-BSA coated graft, the counts were only 97,510/4 minutes. Thus, the shunts coated with S-nitroso-BSA have significantly fewer platelets deposited on its internal surface than the one coated with nitroso-BSA.

EXAMPLE 2

Na Nitroprusside Coated Damaged Arterial Surfaces are Less Thrombogenic

The following experiments demonstrate that nitric oxide-donating compounds, such as sodium nitroprusside and S-nitroso-BSA, can be applied directly to damaged arterial or venous surfaces (blood vessels) to inhibit platelet deposition and thrombus formation.

The inventors developed an animal model which allows them to mimic a patient with narrowing of the coronary or other arteries and arterial damage caused by atherosclerosis or after angioplasty, atherectomy or other procedure. The model uses anesthetized dogs with open chest and exposed heart. Briefly, an electromagnetic flow probe is placed on the coronary artery to continuously measure blood flow through the artery. Then the arterial wall is damaged(intima and media) by clamping the artery several times with a surgical clamp. In the area of arterial damage, a plastic encircling cylinder is placed around the outside of the coronary artery to produce a 70% narrowing or reduction in the lumen gradually diameter. This mimics atherosclerotic narrowing of arteries in patients. Platelet-mediated thrombi periodically form in the stenosed lumen, gradually cutting off the coronary blood flow. Subsequently, the thrombi embolize distally and blood flow is restored. This process, which occurs periodically, produces cyclical reductions in flow, hereinafter referred to as "cyclic flow reductions" (CFRs). If no action is taken to prevent platelet interaction with the damaged arterial wall, these CFRs will continue to occur for many hours.

The inventors have determined that CFRs represent an interaction between platelets and the clotting system, and damaged endothelial cells in narrowed or stenosed arterial walls. In addition, CFRs occur in human arteries which are narrowed by atherosclerosis, and the resulting periodic clot formation can cause chest pain or leg pain in patients with atherosclerotic narrowing of coronary or leg arteries. Finally, the CFRs due to platelet-mediated clotting can be exacerbated by further damage to the arterial wall.

During the course of this study it was observed that when arterial wall was damaged initially by clamping the artery with a surgical clamp, platelet thrombi formed, and CFRS were produced. As a result of this observation, the following experiments were conducted to determine if direct infusion of an NO donor such as sodium nitroprusside can make a damaged arterial wall less thrombogenic.

The following experiments demonstrate that nitric oxide-donating compounds, such as sodium nitroprusside and S-nitroso-BSA can be applied directly to damaged arterial surfaces (blood vessels) to inhibit platelet deposition and thrombus formation.

In five anesthetized dogs, both carotid arteries were exposed. Two 3 FR USC1 catheters were prepared for arterial implantation. One catheter was soaked in a 5% BSA solution for 12 hours, while the other was soaked in a 5%

BSA solution which also contained 1 mg/ml of sodium nitroprusside. One each of the two coated catheters was placed randomly in the right or left carotid artery of the dog through a small incision sealed with a 6-0 proline suture. The catheters were advanced for 5 cm into the arterial lumen. The dogs were not given any heparin. The catheters were removed 6–8 hours later and examined for clotting on the catheter wall and at the site where the catheter entered the carotid wall. There was considerably more clotting on the BSA-coated catheter compared to the catheter coated with BSA plus sodium nitroprusside.

In five open-chested anesthetized dogs, the coronary artery was dissected out and instrumented for measuring CFRs as previously described. The inventors observed that intravenous infusion of sodium nitroprusside directly into the artery (at a dose of between 4 and 10 μg/kg/min. for up to 30 minutes) resulted in a decrease in vivo platelet activity and CFRs were abolished. In addition, the circulating nitroprusside appeared to coat the damaged arterial wall, thus making it less thrombogenic. The CFRs were observed to continue until the sodium nitroprusside infusion had been given for 15 minutes. Then, the CRFs ceased, which suggests that the platelets were no longer adhering to the arterial wall. The sodium nitroprusside intravenous infusion was then stopped. The direct in vivo inhibition of circulating platelets normally stops within 10–15 minutes. However, after the in vivo inhibition of the platelets by the presence of circulating sodium nitroprusside was gone, the CFRs did not return. This indicates that the previously circulating sodium nitroprusside left a protective coating on the previously damaged arterial surface. The inventors have termed this protective coating process "passivation."

The inventors then showed that if one gently rolls the artery between the fingers, the CFRs return immediately. This suggests that the protective coating provided by sodium nitroprusside, has been removed from the internal surface of the previously damaged artery, thus, allowing platelets to resume interaction with the unprotected arterial wall and produce CFRs. In order to demonstrate that this was a local phenomenon affecting the damaged artery, and not due to a systemic effect inhibiting all the circulating platelets, the following experiments were performed.

Open-chest anesthetized dogs were studied. In the dog, and also in humans, the two major branches of the main left coronary artery which are approximately equal in size, are called the left circumflex (circ) and the left anterior descending (LAD), coronary arteries. In the experiments, both branches were instrumented with a flow measuring device, were given equal arterial wall damage (endothelial and medial damage), and had encircling plastic cylinders placed on them to produce equal amounts of narrowing or stenosis.

Following the induction of damage in both coronary arterial branches, CFRs were observed in both the LAD branch and the circumflex branches of the left coronary artery, indicating that the circulating platelets were adhering to both the narrowed part of the damaged circumflex artery and also to the damaged LAD artery. Sodium nitroprusside (10 mg/kg) was then infused directly into the circumflex coronary artery over 30 seconds. Following the infusion, the CFRs in the circ disappeared while they continued in the LAD coronary artery. This demonstrates that the sodium nitroprusside had a local protective effect on the damaged circ, and that the dose of sodium nitroprusside was not high enough to affect circulating platelets or, after recirculation dilution, to protect the damaged LAD wall.

CFRs due to platelets adhering and aggregating on the damaged arterial walls were observed in both arteries, each independent of the other. Therefore, by injecting the sodium nitroprusside into the circumflex branch, the inventors were able to coat this damaged artery directly. In addition, the circulating concentration of sodium nitroprusside remaining after local infusion appears to be too low to have a systemic effect on platelets. Thus, the inventors demonstrated that the protective effect exerted by localized application of sodium nitroprusside is a local effect, and can be applied directly to protect particular segments of a damaged artery.

Experiments identical to those described above were repeated using a nitric oxide-bovine serum albumin adduct (BSA-NO) (with approximately 0.5 mM NO concentration) given selectively into the circumflex coronary artery. The inventors show that using BSA-NO as the No adduct provides better passivation and the effect lasts longer. When the protective BSA-NO coating has been on the damaged arterial wall for 4 to 5 hours, the BSA can be recharged with new NO molecules by infusing sodium nitroprusside intravenously (5–10 μg/kg for 20 minutes) or directly into the coronary artery (10 mg/kg for 30 seconds).

EXAMPLE 3 pS-NO-BSA Treats Vascular Injury

Materials: Sulfanilamide and N-(1-naphthyl) ethylenediamine dihydrochloride were purchased from Aldrich Chemical Co., Milwaukee, Wis. Sodium bicarbonate, sodium chloride, sodium phosphate, sodium nitrite, potassium phosphate-monobasic, 40% formaldehyde solution and sucrose were purchased from Fischer Scientific, Fairlawn, N.J. Sephadex G25 was purchased from Pharmacia, Piscataway, N.J., IODO-BEADS were purchased from Pierce, Rockford, Ill. and Na[$^{125}$I] from New England Nuclear, Boston, Mass. [$^{111}$In] oxine was purchased from Amersham, Arlington Heights, Ill. Monoclonal mouse antiproliferating cell nuclear antigen was purchased from Dako A/S, Denmark. All other chemicals were purchased from Sigma Chemical Co., St. Louis, Mo.

Citrate-phosphate-dextrose anticoagulant solution (CPD) contained 10 mM citric acid, 90 mM trisodium citrate, 15 mM $NaH_2PO_4H_2O$, and 142 mM dextrose, pH 7.35. Tris-buffered saline consisted of 10 mM tris[hydroxymethyl] aminoethane, pH 7.4, and 150 mM NaCl. Acid-citrate-dextrose contained 100 mM trisodium citrate and 142 mM dextrose, pH 6.5. Phosphate-buffered saline contained 10 mM sodium phosphate and 150 mM NaCl, pH 7.4.

Synthesis of S-nitroso-species: S-NO-BSA was synthesized as previously described.[10] Fatty acid-free bovine serum albumin (200 mg/ml) was exposed to a 1.4 molar-fold excess of $NaNO_2$ in 0.5 N HCl for 30 minutes at room temperature and neutralized with an equal volume of TBS and 0.5 N NaOH. Thiolated bovine serum albumin (pS-BSA) was prepared after Benesch and Benesch.[14] Briefly, essential fatty acid-free bovine serum albumin (50 mg/ml) was dissolved in water with N-acetyl-homocysteine thiolactone (35 mM) and 0.05% polyethylenesorbitan monolaurate. Equimolar silver nitrate was slowly added at room temperature over 90 minutes at pH 8.5. Excess thiourea (70 mM) was added and the pH lowered to 2.5. Excess silver nitrate was removed by Dowex 50 chromatography with the mobile phase consisting of 1M thiourea, pH 2.5, and excess thiourea was removed by Sephadex G-25 chromatography. pS-BSA was prepared within two days of nitrosylation and stored at $4^{11}$ C. Nitrosylation of PS-BSA was accomplished with 3.6 mM $NANO_2$ in 0.5 HCl for 30 minutes at room temperature. The solution was adjusted to pH 4.0 with 0.5 NAOH after nitrosylation. In platelet binding studies, 0.1 mM EDTA was added to pS-BSA prior to nitrosylation.

The content of S-nitrosothiol was determined by the method of Saville (Wistow et al., *J. Nucl. Med.* 19:483.–487, 1978). Protein content was determined using the method of Lowry and colleagues (Marcus Salier, *FASEB.J.*, 7:516–522, 1993).

Preparation of [$^{125}$I]-labeled S-NO-BSA and [$^{111}$In] labeled platelets: BSA (0.1 mg/ml) was combined with two IODO-BEADS and 0.1 mCi of Na[$^{125}$I]. The solution was incubated for 45 minutes and unincorporated Na[$^{125}$I] was removed by gel filtration with Sephadex G25 equilibrated with TBS containing 0.1 mg/ml BSA. [$^{125}$I]BSA had a specific activity of $5.7 \times 10^6$ cpm/µg and was S-nitrosylated as described for unlabelled BSA to achieve a final specific activity of $4 \times 10^4$ cpm/mg BSA. [$^{111}$In]-labeling of platelets was performed after the method of Wistow and colleagues.(17)

Animal Preparation: All animal preparations were performed within the institutional guidelines of the Brockton/West Roxbury Department of Veteran Affairs Medical Center and Boston University Medical Center, and in accordance with the guiding principles of the American Physiological Society. New Zealand white rabbits (3.5–4.2 kg) of either sex were premedicated with 5 mg/kg intramuscular (IM) xylazine hydrochlolide (Miles Pharmaceuticals, Shawnee Mission, Kans.), and 0.1 mg/kg subcutaneous (SC) atropine sulfate (Lyphomed, Deerfield, Ill.) fifteen minutes prior to the induction of anesthesia. Anesthesia was induced with 40 mg/kg IM ketamine hydrochloride (Fort Dodge Laboratories, Fort Dodge, Ind.) and 5 mg/kg IM acepromazine maleate (Aveco Company, Inc., Fort Dodge, Ind.). Additional doses of ketamine hydrochloride were administered as necessary to maintain anesthesia. For survival studies, 100,000 U penicillin G (Apothecon of Bristol-Myers Squibb, Princeton, N.J.), was administered IM perioperatively. The skin over the femoral arteries was next infiltrated with 1% lidocaine (Astra Pharmaceuticals, Inc., Westborough, Mass.) and the common femoral arteries were exposed from the inguinal ligament to the superficial femoral artery. Arteries were cleared of connective tissue, side branches were ligated, and the superficial femoral artery was suspended with silk ties. A 1.5-to-2.0 cm length of femoral artery was isolated from the circulation proximally and distally with neurosurgical microaneurysm clips. The superficial femoral-artery was cannulated with a 2F Fogarty balloon catheter (American Edwards Laboratories, Santa Ana, Calif.) that was passed into the isolated segment of femoral artery. The balloon was inflated with sufficient air to generate slight resistance and withdrawn three times. A 20 g angiocath was then inserted in the arteriotomy and 1 ml of 25.8 mg/ml PS-NO-BSA or 49.2 mg/ml S-NO-BSA was administered over 15 minutes. The contralateral femoral artery was prepared identically and an appropriate control (25.8 mglml pS-BSA, 49.2 mg/ml BSA or 0.66 mg/ml sodium nitroprusside) was administered. For binding studies, 0.5 ml of [$^{125}$I]-labeled nitrosylated albumin or control was administered. Following administration of the agent, the superficial femoral artery was ligated and flow reestablished. Sham-operated animals underwent surgical exposure and sidebranch ligation, but no balloon injury was performed or local delivery administered. The area of balloon injury was marked by surgical staples in the adjacent muscle fascia. For chronic studies, the incision was closed with subcuticular absorbable suture and the animals allowed to recover. For acute studies, blood was allowed to circulate through the treated areas for 15 minutes prior to vessel harvest. In some experiments, a distant control vessel, the right carotid artery, was isolated and harvested without any other manipulation.

cGMP analysis: Whole blood was obtained from fasting human volunteers and platelet-rich plasma (PRP) was prepared by centrifugation. Platelet counts were determined using a Coulter counter model ZM (Coulter Diagnostics, Hileah, Fla.). After balloon injury and treatment with pS-NO-BSA or PS-BSA, arterial segments were harvested and 2-mm segments were incubated with 100 µl of PRP containing 10 µM isobutylmethylxanthine. After 1 minute, an equal volume of ice-cold 10% trichloroacetic acid was added to each aliquot and the sample vortexed. Enzyme-linked immunoassay of cGMP was then performed (Cayman Chemical Company, Ann Arbor, Mich.). Separate 2 mm vessel segments were also assayed for tissue CGMP after treatment with ice-cold 10% trichloroacetic acid and sonication (Heat Systems-Utrasonics, Inc., Plainview, N.Y.).

Tissue processing and analysis: On the 14th postoperative day, animals were euthanized with 120 mg/kg intravenous sodium pentobarbital (Anpro Pharmaceuticals, Arcadia, Calif.), and the abdominal aorta and inferior vena cava interrupted by silk ties. A 7F plastic cannula was inserted into the abdominal aorta and the vessels perfused clear with saline followed by fixation at 100 mm Hg pressure with 10% buffered formalin. The vessels were stored in 10% buffered formalin and the samples paraffin-embedded and microtome-sectioned. Six sections were made along the length of each injured segment of vessel and stained with Verhoeff's stain for elastic tissue. The areas within the lumen, internal elastic membrane, and external elastic membrane were measured by a blinded observer using computerized digital planimetry (Zeiss, West Germany). The areas within the lumen, internal elastic membrane and external elastic membrane were analyzed. Sections with obstructive thrombus impairing analysis were discarded.

In a separate set of animals, vessels were perfusion-fixed with 10% buffered formalin seven days after injury and processed for analysis of proliferating cells within 12 hours as described above. Sections were stained for proliferating cell nuclear antigen and adjacent sections were stained with hematoxylin and eosin. Five representative sections from each segment were examined. Total nuclei were counted from the hematoxylin and eosin slides and percent PCNA positive cells were defined as the number of PCNA-positive nuclei divided by the total number of nuclei multiplied by 100.

[$^{111}$In]-labeled platelet studies: Animals were prepared and treated with pS-NO-BSA or pS-BSA as described above. Five minutes prior to the release of the vascular clamps, autologous [$^{111}$In]-labeled platelets were infused via the femoral vein, and the blood was allowed to recirculate for 15 minutes prior to harvest. Platelet adhesion was quantified with a gamma counter (Capintec Instruments, Inc., Pittsburgh, Pa.) and normalized to tissue wet weight.

Statistics. Data are presented as mean +/− SEM. Treatments were administered in a paired fashion with one femoral artery receiving S-nitrosylated protein and the contralateral artery receiving the appropriate non-nitrosylated control. Sodium nitroprusside was given to a separate set of animals. Data were tested for normality using the Kolmogorov-Smirnov algorithm and for equal variance with the Levene Median test. Normally distributed variables were compared using the paired t-test and non-normally distributed variables using the Wilcoxon sign-ranks. test or the Mann-Whitney rank-sum test. Non-paired data were compared using an independent t-test. Statistical analysis of dose-response was performed by one-way analysis of variance. Statistical analysis of dose-response was performed by one-way analysis of variance. Statistical significance was accepted if the null hypothesis was rejected with P<0.05.
Results NO content of S-nitrosothiol species: The synthesis of S-NO-BSA resulted in a final protein concentration of 755 $\mu$M (49.2 mg/ml) and yielded a displaceable NO content of 230±60 $\mu$M, yielding a stoichiometry of 0.3+/−0.08 moles NO/mole albumin (n=11). Thiolation and S-nitrosylation of BSA produced a final protein concentration of 391 $\mu$M (25.8 mg/ml, n=8) and yielded a 5.9-fold increase in displaceable NO content with a maximum content of 2300 $\mu$M displaceable NO as compared to S-NO-BSA. Local delivery consisted of 1 ml of either S-nitrosylated protein or control solution instilled in the lumen of the femoral artery.

Figure 3:
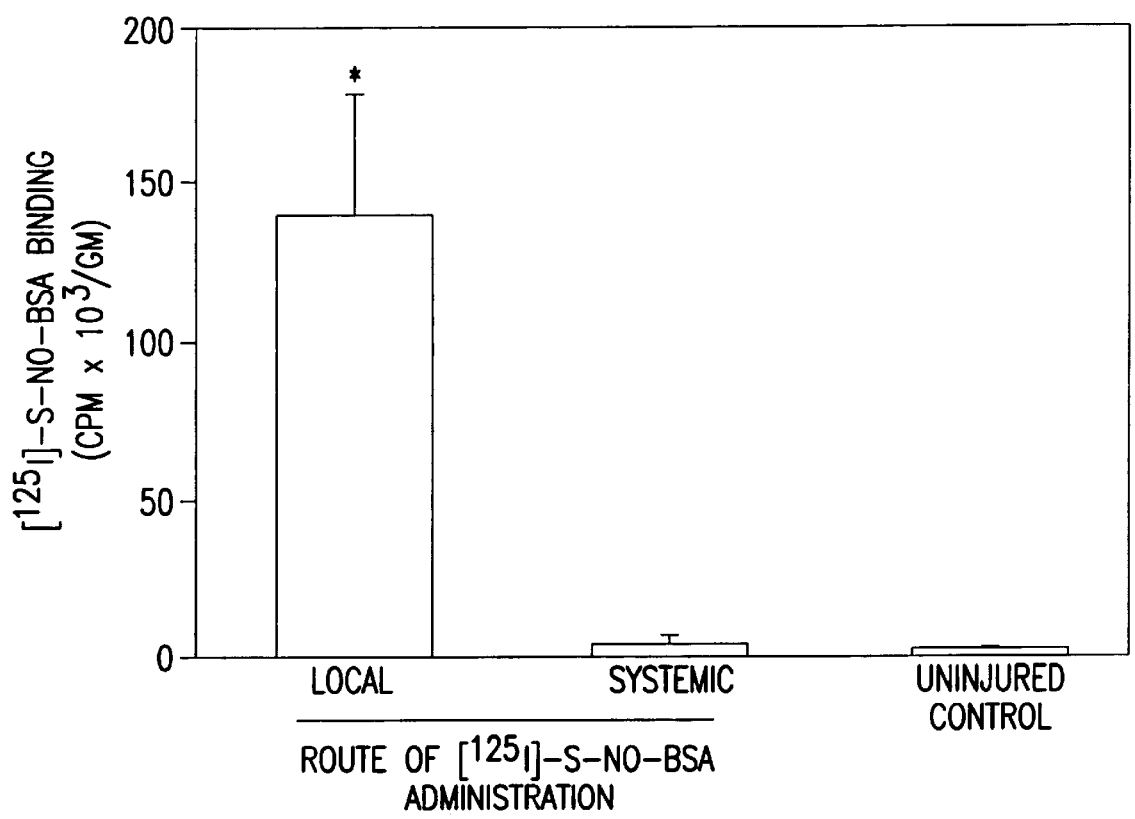
FIG. 3 is a plot demonstrating [$^{125}$I]-labeled S-nitroso-albumin [$^{125}$I]-S-NO-BSA) binding to injured rabbit femoral artery as a function of the method of delivery. Rabbit femoral arteries were isolated and balloon-injured as described in Example 1 and [$^{125}$I]-S-NO-BSA applied either directly into the injured artery (local) or injected intraarterially via the opposite femoral artery (systemic). [$^{125}$I]-S-NO-BSA binding was determined by quantification of radioactivity after flow was reestablished for a period of 15 minutes. Non-specific [$^{125}$I]-S-NO-BSA binding (sham) was determined from uninjured carotid artery harvested simultaneously with femoral arteries. Data are presented as mean +/− SEM per gram of wet tissue weight, and are derived from four animals. *P<0.0.029, local vs. systemic delivery and +/+P<0.05, systemic injured vs. sham.
Figure 4:
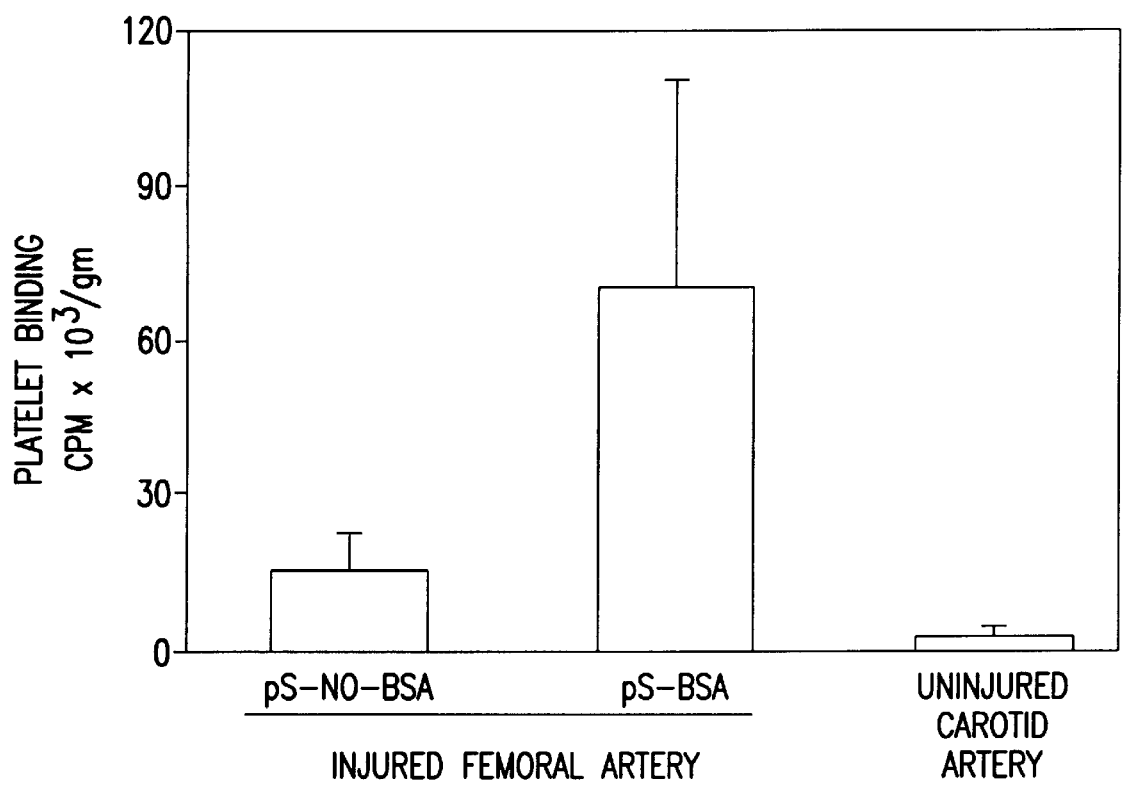
FIG. 4 is a plot demonstrating the effect of polythiolated S-nitroso-albumin (pS-NO-BSA) and polythiolated albumin (pS-BSA) on [$^{111}$In]-labeled platelet binding to injured rabbit femoral arteries. Femoral arteries were isolated and balloon injured as described in Example 1. During paired local administration of polythiolated S-nitroso-albumin and polythiolated albumin, [$^{111}$In]-labeled platelets were administered intravenously and allowed to circulate after flow was reestablished in the treated arteries. [$^{111}$In]-labeled platelet binding was determined by quantification of radioactivity after flow was re-established for a period of 15 minutes. Non-specific [$^{111}$In]-labeled platelet binding (Uninjured Carotid Artery) was determined from uninjured carotid artery harvested with femoral arteries. Data are presented as mean +/− SEM per gram of wet tissue weight and are derived from six animals. *P<0.05, PS-BSA vs. pS-NO-BSA.

S-NO-BSA binding: The binding of locally and systemically delivered [hu 125I]-labeled S-NO-BSA to balloon-injured rabbit femoral artery is shown in FIG. 3 Compared with systemic administration to an injured artery, local delivery of [$^{121}$I]-S-NO-BSA to the site of injury was associated with a 26-fold increase in binding (140.4+/−3.9× $10^3$ cpm/gm vs. 5.4+/−0.9×$10^3$ cpm/gm, n=4; P=0.029). Endothelial denudation facilitated S-NO-BSA binding as systemic administration of [$^{121}$I]-S-NO-BSA resulted in significant deposition at the site of balloon injury compared to an uninjured control vessel exposed to systemically delivered [$^{125}$I]-S-NO-BSA (5.4±0.9×$10^3$ cpm/gm vs. 3.0+/−0.3 cpm/gm, n=4 ; P=0.038).

pS-NO-BSA effect on platelet binding to injured vessel: Since platelet adhesion to the injured arterial surface is important in the proliferative response to injury, we investigated the effects of pS-NO-BSA on platelet deposition after balloon injury, the results of which are shown in FIG. 4. The local administration of pS-NO-BSA reduced the adhesion of [$^{111}$In]-labelled platelets to the injured vessels over four-fold compared to control (71.3+/−40.4×$10^3$ cpm/gm, n=6, vs. 16.3+/−6.2×$10^3$ cpm/gm, n=6, P=0.031).

Figure 5A:
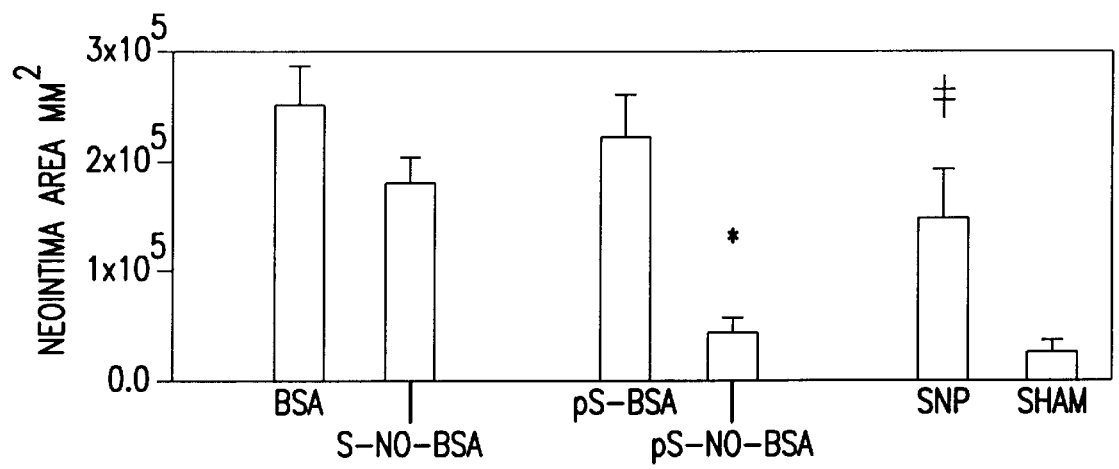
FIGS. 5A–5B are plots demonstrating the effect of polythiolated S-nitroso-albumin (pS-NO-BSA) and polythiolated albumin (pS-BSA) on neointimal proliferation 14 days after balloon injury of rabbit femoral artery. Femoral arteries were isolated and balloon injured as described below. pS-BSA or pS-NO-BSA were applied in a paired fashion directly into the arterial lumen for 15 minutes and then blood flow was re-established. After 14 days, arteries were harvested, perfusion-fixed, stained, and subjected to morphometric analysis of intimal and medial areas. Neointimal proliferation is reported as the absolute neointimal area in FIG. 5A and as a ratio of neointima/media in FIG. 5B in 4–6 segments from each artery. Data are expressed as mean +/− SEM and are derived from 15 vessels in the BSA and S-NO-BSA groups, 11 vessels in the PS-BSA group, 7 vessels in the PS-NO-BSA and SHAM groups, and 5 in the SNP group. *P<0.05, pS-NO-BSA vs. PS-BSA. +/+P<0.05 Sodium nitroprusside vs. pS-BSA for both FIGS. 5A and 5B.
Figure 5B:
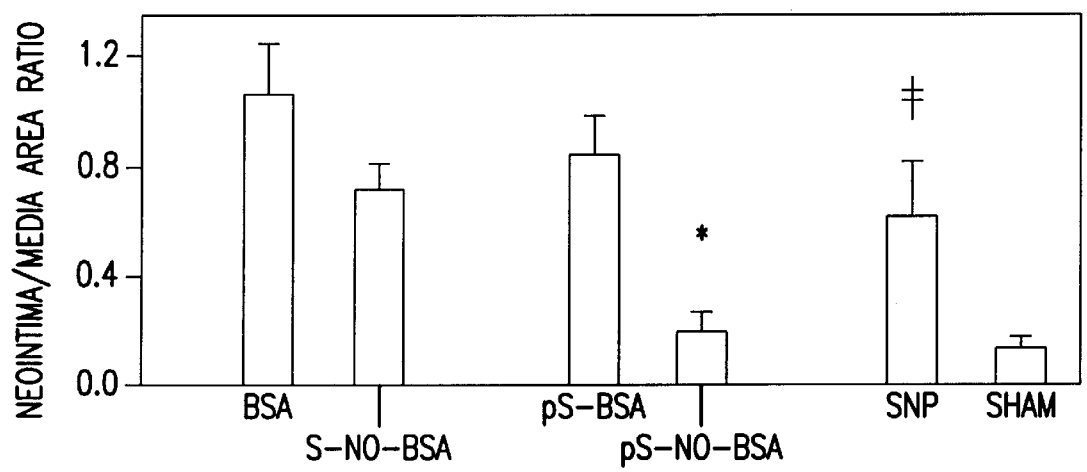

S-NO-BSA and pS-NO-BSA effects on neointimal proliferation: Neointimal proliferation after local delivery of S-nitrosylated proteins and appropriate controls were evaluated by comparing absolute neointimal area and neointima/media ratios, and are shown in FIGS. 5A and 5B, respectively. The administration of S-NO-BSA (containing 0.3±0.1 moles diplaceable NO per mole albumin) did not significantly reduce neointimal area (2.54+/−0.33×$10^5$ $\mu$m$^2$ vs. 1.83+/−0.18×$10^5$ $\mu$m$^2$, n=15) or neointima/media ratio (1.07+/−0.167 vs. 0.72+/−0.084, n=15) 14 days after balloon injury, although a trend was noted. By contrast, the administration of pS-NO-BSA (containing 3.2±1.3 moles displaceable NO per mole albumin) with a greater displaceable NO content did reduce neointimal area and neointima/media ratio by 81% (2.24+/−0.328×$10^5$ $\mu$gm$^2$ vs. 0.41+/−0.11×$10^5$ $\mu$m$^2$, n=7, P=0.022) and 77% (0.85+/−0.122 vs. 0.196 +/−0.66, n=7, P=0.025), respectively. The neointimal area (0.23+/−0.07×$10^5$ $\mu$m$^2$) and neointima/media ratio (0.116+/−0.041, n=7) in the sham operated animals were comparable to those of the vessels treated with pS-NO-BSA. Using relatively high concentrations of a conventional No donor, SNP (2300 $\mu$M), we noted a trend towards inhibition of neointimal proliferation in both neointimal area (1.47 +/−4.15×$10^5$ $\mu$M$^2$, P=0.056) and neointima/media ratio (0.603+/−0.19, n=5, P=0.11) compared to control.

pS-NO-BSA effects on cellular proliferation: Mouse monoclonal antibody staining against PCNA was used to assay the degree of Sl-phase activity at 7 days after injury. At this time, no difference in the percent of proliferating cells was noted between vessels treated with pSBSA (30.1% +/−5.9, n=5) and vessels treated with pS-NO-BSA (37.8% +/−5.9, n=6). Similarly, no significant difference was noted in the neointimal proliferation of the pS-NO-BSA-treated vessels compared to the pS-BSA-treated controls (neointimal area: 0.124±0.06×$10^5$ $\mu$M$^2$ vs. 0.258+/−0.19× $10^5$ $\mu$m$^2$, n=5, P=0.54, and neointima/media ratio: 0.032±0.005 vs. 0.068±0.027, n=5, P=0.15).

Figure 6A:
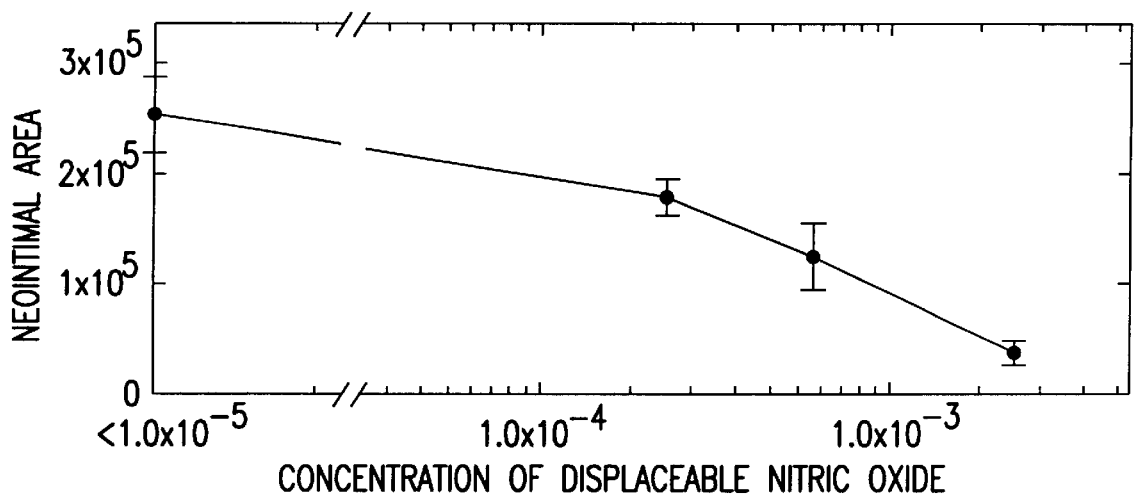
FIGS. 6A–6B are plots demonstrating the relationship between neointimal proliferation and the quantity of displaceable NO in preparations of S-nitrosylated albumin. Femoral arteries were isolated and balloon injured as described with reference to FIG. 5. Vessels were exposed to different preparations of S-nitrosylated albumin with different displaceable No contents. After 14 days vessels were harvested and analyzed as described in FIG. 5. Data are expressed as mean +/− SEM and are derived from 7–15 animals in each group. P<0.001 for trend.
Figure 6B:
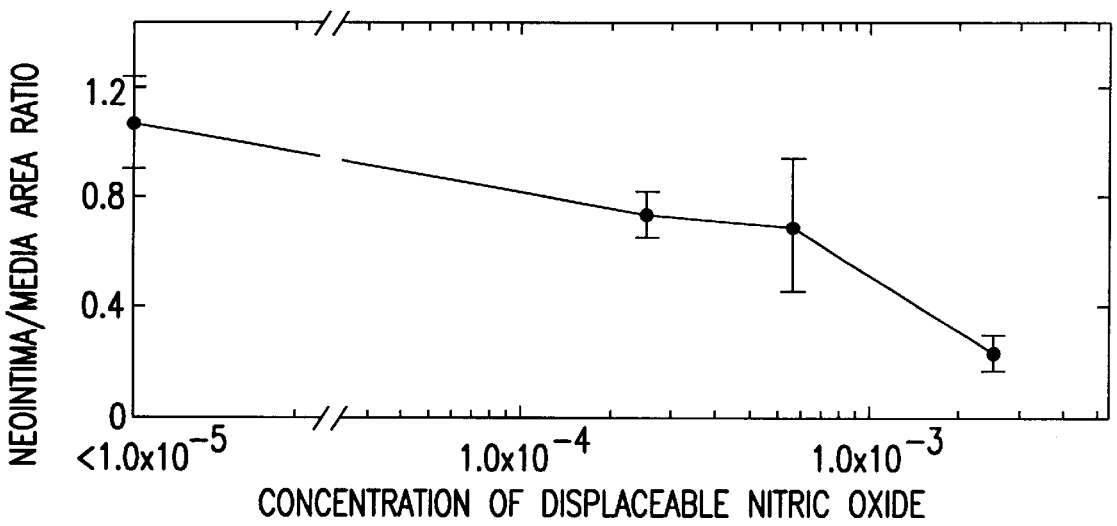
Figure 7:
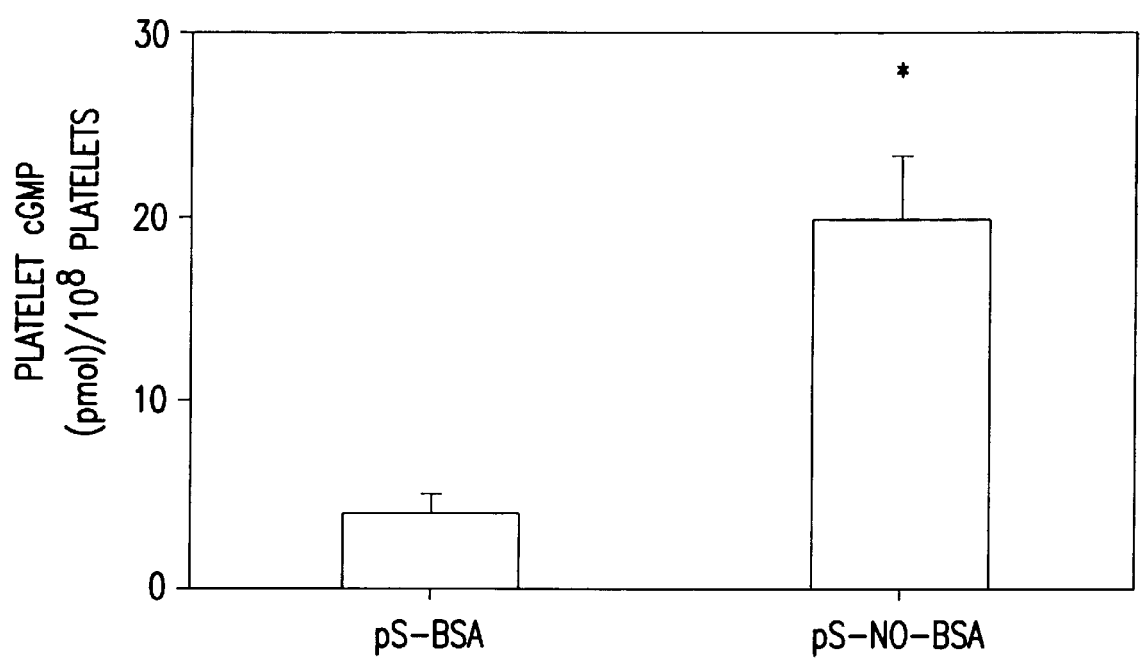
FIG. 7 is a plot demonstrating the effect of polythiolated S-nitroso-albumin (pS-NO-BSA)- and polythiolated albumin (pS-BSA)-treated vessels on platelet cyclic 5'-3' guanosine monophosphate (cGMP). Rabbit femoral arteries were isolated and balloon-injured as described with reference to FIG. 4. After paired local administration of polythiolated S-nitroso-albumin and polythiolated albumin for 15 minutes, the vessels were harvested and divided into 2 mm rings. The rings were then immersed in 100 µl of platelet-rich plasma containing 10 µM 3-isobutyl-1-methylxanthine and were incubated for 1 minute ex-vivo. An equal volume of ice-cold 10% trichloroacetic acid was added to each aliquot and the sample vortexed. Platelet cGMP assay was then performed as described in "Methods." Data are expressed as mean +/− SEM. *P<0.05.

Displaceable NO effect on neointimal proliferation: Since S-NO-BSA exhibited a trend toward inhibition and pS-NO-BSA reduced neointimal proliferation, we examined the relationship between the amount of displaceable No and the extent of neointimal response following vascular injury, and the results are presented in FIGS. 6A and 6B. There was a significant inverse relationship between displaceable NO and neointimal proliferation as quantified by absolute neointimal area (P<0.001) (FIG. 6A) and the neointima/media area ratio (P<0.001) (FIG. 6B).

pS-NO-BSA treated vessel effect on platelet GMP and vessel GMP: NO inhibits platelets and relaxes smooth muscle cells through a cGMP-mediated mechanism. We tested the ability of pS-NO-BSA-treated vessels to deliver NO to platelets, and these results are shown in FIG. 7. Platelet cGMP was significantly increased after a one-minute exposure to pS-NO-BSA-treated vessels compared to PS-BSA controls (19.9+/−3.3 vs 4.11+/−0.9 pmol $10^8$ platelets, n=14, P<0.001). In addition, vessel cGMP levels were also elevated after treatment with pS-NO-BSA compared to PS-BSA control (0.48+/−0.46 vs 0.283+/−0.23 pmol/mg protein, n=3) suggesting a direct effect on vascular smooth muscle cells, as well.

Discussion

We have previously demonstrated that No combines with protein sulfhydryl groups to form stable, biologically active molecules with cGMP-dependent vasodilatory and anti-platelet properties, both in vitro and in vivo (Stamler et al., *Proc. Natl. Acad. Sci. U S A.*, 89:444–448, 1992); (Weldinger et al., Circulation, 81:1667–1679, 1990). The data presented here demonstrate that serum albumin, after S-nitrosylation, can bind avidly to balloon-injured femoral. arteries and inhibit neointimal proliferation. This phenomenon is associated with diminished platelet deposition at the site of injury through a cGMP-dependent mechanism. Moreover, the extent of inhibition of neointima formation is directly related to the quantity of displaceable NO carried by albumin.

The endothelium is essential for vascular integrity, control of thrombosis, (Clowes et al., *Lab. Invest.* 49:327–333, 1983); (Rees et al., *Proc. Natl. Acad. Sci. USA*. 86:3375–3378, 1989) and the regulation of intimal growth (Kubes et al., *Proc. Natl. Acad. Sci. USA,* 88:4651–4655, 1991). The endothelium serves these functions by the production of locally active effector molecules including EDRF, a compound that has been identified as NO or a closely related molecule. EDRF is responsible, in part, for many biologic actions via the activation of guanylyl cyclase, including relaxation of vascular smooth muscle, (Myers et al., *Nature (Lond.)*, 345:161–163, 1990); (Kubes and Granger, *Am. J. Physiol.* 262:H611–H615, 1993) inhibition of platelets, (Radomski et al., *Br. J Pharmacol,* 92:181–187, 1987) control of leukocyte adhesion to the subendothelium, (Reidy, *Lab. Invest.,* 5:513–520, 1985) modulation of vascular permeability, (Groves et al., *Circulation,* 87:590–597, 1993) and, perhaps, local control of vascular smooth muscle growth. Since balloon angioplasty removes the endothelium from arterial smooth muscle, these endothelial functions are lost during the procedure. In particular, removal of the endothelium and damage to the smooth muscle cells are associated with intimal proliferation (McNamara et al., *Biochem. Biophys. Res. Commun.,* 193:291–296, 1993). The mechanism for this response is complex and involves platelet deposition and activation, cytokine elaboration, smooth muscle cell migration and proliferation, and extra-cellular matrix production. After balloon injury, the endothelium regenerates rapidly but is often dysfunctional, and presumably unable to maintain an adequate antithrombotic, vasodilating, and antiproliferative phenotype (Saville, *Analyst* 83:670–672, 1958).

NO donors have been used with some success in the setting of balloon injury to produce decreases in intimal proliferation and in platelet deposition. In the porcine carotid model, Groves and colleagues (Kubes and Granger, *Am. J. Physiol.* 262:H611–H615, 1993) demonstrated reduced platelet adhesion and thrombus formation locally after systemic administration of SIN-1, a spontaneous NO donor and metabolite of molsidomine. These authors showed a 2.3-fold reduction in platelet deposition without any significant hemodynamic changes. Because administration of this agent was associated with an increase in template bleeding time and in platelet cGMP, it is possible that SIN-1 exerted its effects through systemic platelet inhibition. A preliminary report from the ACCORD trial also suggests that NO donors might be effective adjuncts for balloon angioplasty in humans (The ACCORD Study Investigators, *J. Am. Coll. Cardiol.* 23:59A. (Abstr.), 1994). This multicenter study evaluated SIN-1 acutely and molsidomine chronically over six months with diltiazem treatment as a control arm in patients undergoing balloon angioplasty. The loss index and binary restenosis rate were significantly improved in the NO treatment group, although the rate loss was not significantly different between groups. Chronic supplementation with L-arginine, a precursor of endothelium-derived nitric oxide, has been shown to reduce intimal hyperplasia in rabbit thoracic aorta (Cayatte et al., *Arterioscler. Thromb.,* 14:7S3–9, 1994) and the rat carotid artery (von der Leven et al., *Clin. Res.,* 42:180A. (Abstr.), 1994). By contrast, administration of an inhibitor of NO synthase, $N^G$-nitro-L-arginine methyl ester, accelerated neointimal formation in the setting of balloon injury (Taubman, wall injury., *Thromb. Haemost.,* 70:180–183, 1993).

von der Leven and Dzau recently reported (Zeiher et al., *Circulation,* 88:1–367. (Abstr.), 1993) successful transfection of the constitutive endothelial-type nitric oxide synthase (eNOS) gene in a rat carotid injury model. In that preliminary study, eNOS incorporation and NO production were demonstrable four days after transfection, and neointimal proliferation was partially inhibited two weeks after injury and transfection. In our study, S-nitrosylated albumin was administered acutely and, given its half-life of 12 hours, (Benesch and Benesch, *Proc. Natl. Acad. Sci. USA,* 44:848–853, 1958 it is unlikely that significant amounts of displaceable NO were still present four days after injury. The effectiveness of both early and late administration of NO suggests that NO may influence the complex response to injury by multiple mechanisms. In addition to modifying the development of platelet thrombus and the release of growth factors from platelets, local delivery of S-nitrosothiols could modulate gene transcription in vascular smooth muscle cells (Lefer et al., *Circulation,* 88:1–565. (Abstr.), 1993) as well as smooth muscle metabolism following injury.

Our data demonstrate a profound limitation of neointimal proliferation after a single, local administration of a durable, potent S-nitrosothiol. Antiplatelet activity may explain these findings, in part, since we observed a four-fold reduction in platelet deposition to injured arterial segments after treatment with pS-NO-BSA. Similarly, we also demonstrated direct platelet inhibition by the pS-NO-BSA-treated vessel rings. Inhibition of platelet binding would result in many effects that are likely to reduce the proliferative response after injury. For example, platelet adhesion and aggregation is associated with the release of PDGF, basic fibroblast growth factor, epidermal growth factor, and transforming growth factor-β, potent stimuli for smooth muscle cell proliferation and matrix production. pS-NO-BSA could also exert its effect by modulating leukocytes though downregulated expression of either monocyte chemoattractant protein-1 (Hanke et al., *Circ. Res.,* 67:651–659, 1990) or adhesion molecules (Lefer et al., *Circulation,* 88:1–565. (Abstr.), 1993). We cannot exclude a direct inhibitory effect of NO on vascular smooth muscle gene expression, migration, proliferation or synthesis of extracellular matrix.

The demonstration of unaltered PCNA-positive cells in vessels treated with pS-NO-BSA compared to control vessels is intriguing. Hanke demonstrated significant DNA synthesis in the neointima and media of a rabbit carotid model using electrical stimulation. Maximal DNA synthesis occurred at approximately seven days (Hanke et al., *Circ. Res.,* 67:651–659, 1990) and lasted until at least fourteen days. Our observations suggest a mechanism other than the inhibition of local cell replication by which to explain the inhibition of neointimal proliferation in the rabbit injury model. Such mechanisms could include an early effect on vascular smooth muscle cell migration, transient inhibition of DNA synthesis which is not evident on day seven after injury, inhibition of extracellular matrix production, or inhibition of another factor(s) required for neointima formation.

These findings have several implications for the treatment of human disease. Mechanical removal of the endothelium abolishes the vasodilator responses to endothelium-dependent vasoactive stimuli, while leaving the vasoconstrictor effects of agonists to smooth muscle unopposed (Furchgott Zawadzki, *Nature (Lond.).* 288–373–376, 1980). This process occurs with balloon angioplasty especially at sites where platelet thrombus is noted (Uchida et al., *Am. Heart. J.,* 117:769–776, 1989); (Steele et al., *Circ. Res.,* 57:105–112, 1985). The strategy of local replacement of an important endothelial product as therapy for acute thrombotic phenomena and restenosis following angioplasty is, thus, suggested by our study.

In summary, our results demonstrate that a stable NO adduct of serum albumin binds avidly to balloon-injured subendothelium when delivered locally. When modified to carry multiple NO groups, pS-NO-BSA markedly decreases neointimal proliferation after balloon injury. Local delivery of this molecule decreases platelet adhesion to the injured subendothelium-and directly inhibits the platelet, interrupting a common pathway through which growth responses are initiated. These results support the hypothesis that local supplementation of a long-acting No donor can favorably modulate vascular injury. The implications of these findings suggest that local delivery of S-nitrosothiols may be an effective treatment for disease states marked by abnormal or absent endothelium, including restenosis after angioplasty.

EXAMPLE 4

Porcine Anqiographic Stenosis Model

Pigs were subjected to coronary balloon-injury using standard methods, in accordance with the protocol illustrated in FIG. 8. A perforated drug delivery balloon catheter was used at the time of balloon injury for infusion of polythiolated, polynitrosated albumin and with albumin control, each of which were infused at a concentration of 1.5 $\mu$M for a period of 15 minutes. The balloon of the catheter was then deflated and the catheter was removed. Thereafter, another angiogram was performed to determine, at 30 minutes after injury, the degree of spasm. Then all catheters were removed and the incision sites were repaired. The animals were awakened and maintained with normal chow diets over the next four weeks. At the end of that period of time, the animals were again sedated, underwent coronary angiography to determine coronary stenoses at the site of angioplasty, after which they were euthanized by an overdose of pentobarbital. Their coronary arteries perfusion fixed with 100 mm Hg of perfusion pressure. They were fixed with formalin, harvested and sectioned for quantitative morphometric assessment of the lumen diameter, the neointimal dimension and cross-section, as well as the neointimal area. The arteries were stained with hematoxylin and eosin. The neointima to lumen diameter ratio was determined and is illustrated by comparison in FIG. 9.

In this study, a number of normal cholesterolomic pigs were subjected to angioplasty and the effect on their coronary artery was evaluated in groups which received ps-NO-BSA and which received pS-BSA as a control or placebo. Four weeks after angioplasty, the animals were sacrificed, their coronary arteries were recovered with perfusion fixation of the artery at autopsy.

Figure 9:
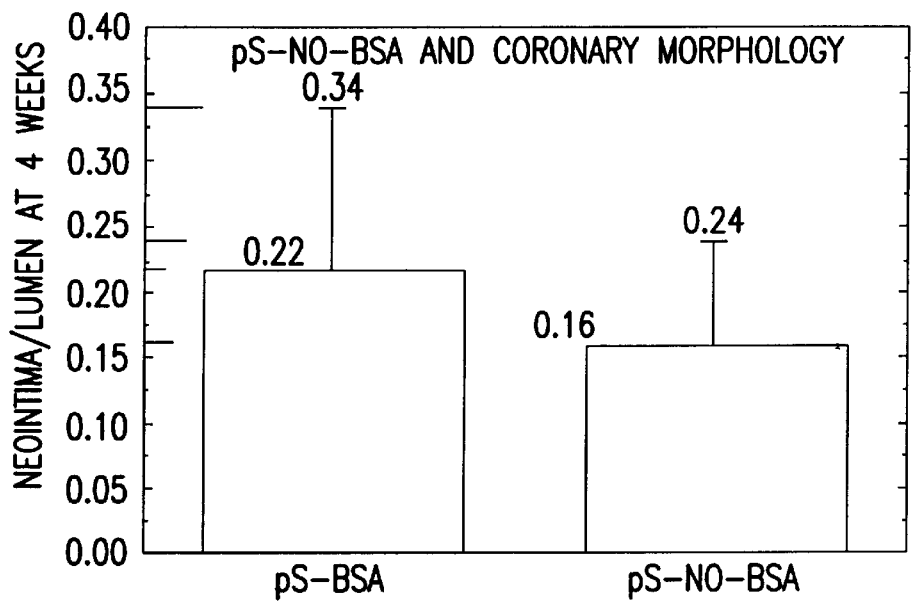
FIG. 9 is a histogram which illustrates the diameter (mm) of the neointimal lumen of 14 normocholesterolemic pigs were subjected to a balloon angioplasty which induced injury of the right coronary artery. Thereafter, they received 1.5 µM pS-NO-BSA or pS-BSA as a control.

FIG. 9 is a histogram which illustrates the diameter (mm) of the neointimal lumen of 14 normocholesterolemic pigs which were subjected to a balloon angioplasty which induced injury of the right coronary artery. Thereafter, they received 1.5 $\mu$M pS-NO-BSA or pS-BSA as a control.

This measurement was made at four weeks into the protocol by coronary angiography. The animals were sedated, catheters were placed in the coronary ostea and radiocontrast fluid was infused. The angiograms were recorded and subsequently processed by a computer-driven quantitative coronary angiography algorithm to determine precisely the lumen diameter. The degree of stenosis represents the percentage reduction in the lumen diameter compared with a reference segment proximal to the area of stenosis using standard methods. The results of this are illustrated in FIG. 10.

Figure 10:
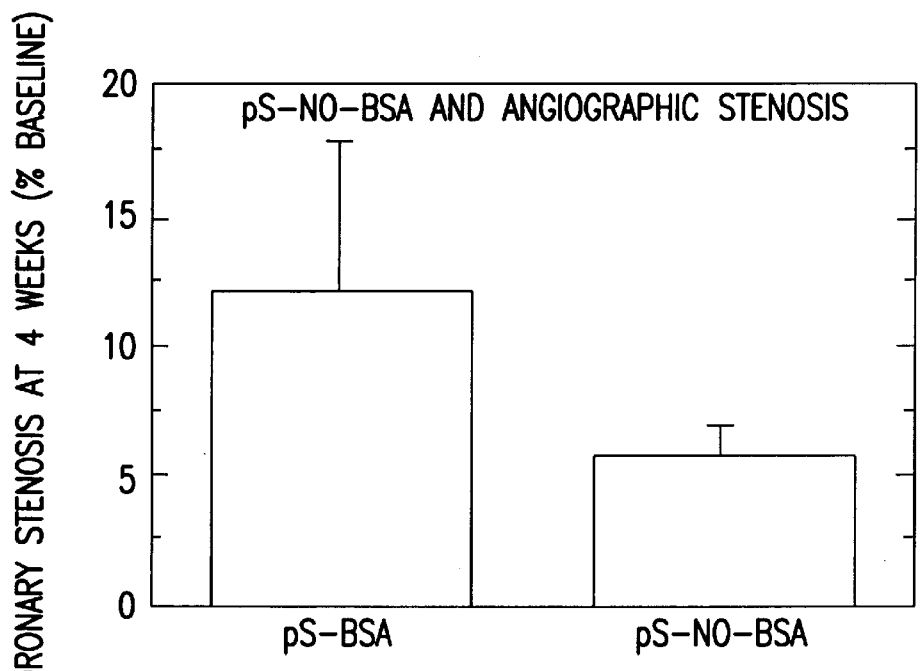
FIG. 10 is a histogram which illustrates a degree of coronary stenosis observed at four weeks after angioplasty in pigs which received 1.5 µM pS-NO-BSA or pS-BSA as a control.

FIG. 10 is a histogram which illustrates a degree of coronary stenosis observed at four weeks after angioplasty in pigs which received 1.5 $\mu$M pS-NO-BSA or pS-BSA as a control.

This measurement was made during the initial balloon injury procedure. Within 30 minutes following the procedure, the animals underwent coronary angiography, coronary catheters were placed in the coronary ostea, radiocontrast was infused into the coronary arteries and measurements were made of the degree of so-called "recoil spasm" that existed at the point of angioplasty. The degree of spasm or recoil was defined quantitatively, again using the computer-driven quantitative coronary angiography algorithm that compared the segment at the site of balloon injury with a proximal segment that was uninjured as a reference standard. The results are illustrated graphically in FIG. 11.

Figure 11:
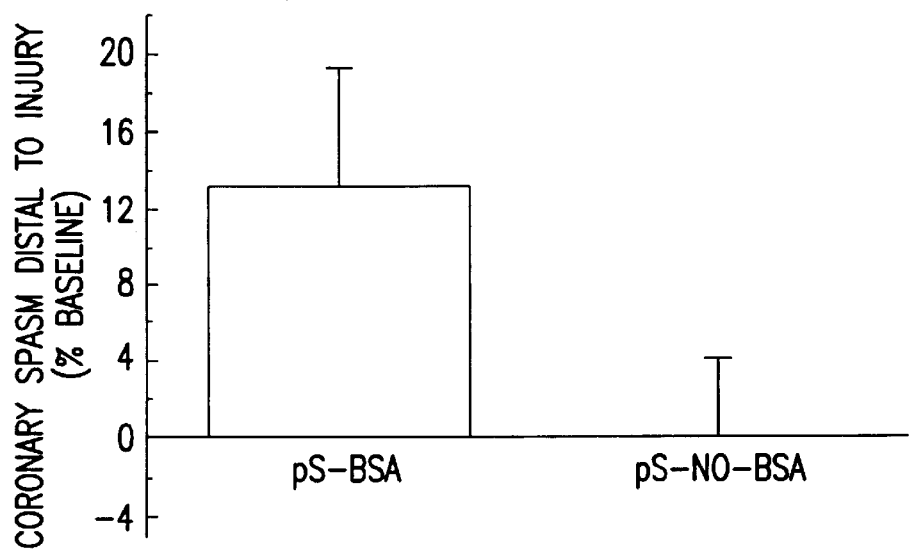
FIG. 11 is a histogram which illustrates the extent of coronary spasm induced distal the site of injury as compared to the pre-existing base line in pigs which received 1.5 µM pS-NO-BSA or pS-BSA as a control.

FIG. 11 is a histogram which illustrates the extent of coronary spasm induced distal the site of injury as compared to the pre-existing base line in pigs which received 1.5 $\mu$M pS-NO-BSA or pS-BSA as a control.

Next, a quantitative measurement was made by morphometric assessment following autopsy and after perfusion fixation of the vessel to determine lumen diameter at four weeks. The results are illustrated in FIG. 12.

Figure 12:
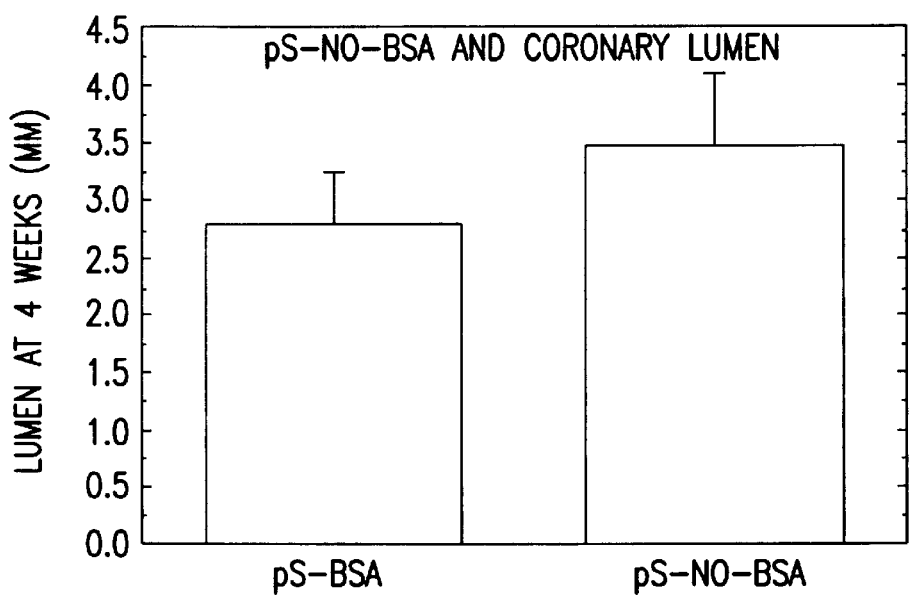
FIG. 12 is a histogram which illustrates the inner-diameter of the lumen of the right coronary artery of pigs four weeks after they received 1.5 µM pS-NO-BSA or pS-BSA as a control.

FIG. 12 is a histogram which illustrates the inner-diameter of the lumen of the right coronary artery of pigs four weeks after they received 1.5 $\mu$M pS-NO-BSA or pS-BSA as a control.

EXAMPLE 5

Coating Palmaz-Schatz Stents with pS NO-BSA

The experiments recorded here were performed in order to determine: whether this pS NO-BSA would adhere to the metallic surface of a Palmaz-Schatz stent; whether there would be enough nitric oxide available to inhibit platelet adhesion and aggregation near the metallic surface; whether coating of a Palmaz-Schatz stent with pS NO-BSA would significantly reduce the deposition of Indium[111]. labeled platelets when placed in the carotid arteries of pigs; whether coating a Palmaz-Schatz stent would decrease the degree of anticoagulation needed to maintain patency; and whether the coating would reduce the degree and severity of neointimal hyperplasia leading to restenosis.

Palmaz-Schatz stents were dip-coated in 800–1000 $\mu$M SNO-BSA three times for 10 minutes followed by 10 minutes of air drying time. Then, one week later, three coated stents were immersed in platelet rich plasma (PRP) for 2 minutes. A control uncoated stent was also immersed in another aliquot of the same PRP.

The increase in platelet cyclic GMP levels was determined and is shown in Table 1.

TABLE 1

Cyclic GMP Levels in PRP Exposed for 2 Minutes to pS NO-BSA Coated and Uncoated Palmaz-Schatz Stents

| | (P moles CGMP/$10^8$ platelets) | | | |
|---|---|---|---|---|
| Conc of NO (Saville $R_x$) | A | B | C | D |
| 500 $\mu$M | 7.2 | 6.8 | 6.9 | 6.3 |
| | 7.0 | 6.0 | 6.8 | 4.6 |
| | 2.8 | 2.8 | 2.4 | 1.7 |
| 800 $\mu$M | 5.8 | 5.6 | 5.9 | 3.9 |
| | 10.4 | 11.0 | 10.8 | 8.5 |
| 1000 $\mu$M | 4.6 | 4.9 | 5.7 | 1.9 |
| | 6.6 | 5.9 | 6.3 | 3.0 |
| | 5.9 | 5.1 | 5.7 | 2.9 |

The three columns on the left (columns A through C) show the levels of cGMP in the platelets which were exposed to a coated stent and the column on the right (Column D) shows the level of cyclic GMP in the same PRP which was exposed to the uncoated stent.

A coated and an uncoated stent were placed in the carotid arteries of pigs, one in each carotid artery. Then Indium[11] labeled platelets were circulated for four hours. At the end of the four hours, the arteries containing the stents were removed and placed in a Gamma counter well. The counts on stents indicate the degree of platelet deposition on each stent. The data is shown in Table 2.

TABLE 2

Indium[III] Labeled Platelet Counts an S-No-BSA Coated Versus Uncoated Palmaz-Schatz Stents

| P S NO-BSA Coated | Uncoated | Ratio |
| --- | --- | --- |
| 59,760 | 1,076,300 | 18 |
| 94,000 | 246,000 | 2.6 |
| 126,400 | 868,600 | 6.0 |
| 61,500 | 347,400 | 5.7 |
| 120,000 | 684,000 | 5.6 |
| 88,600 | 264,462 | 3.0 |
| 135,000 | 590,000 | 4.1 |
| 14,160 | 43,900 | 3.2 |

One coated and one uncoated stent was placed in each of the two carotid arteries under sterile conditions in 10 pigs They will be followed for 28 days and then the stented carotid arteries will be removed. They will be examined histologically for the degree of neointimal hyperplasia

What is claimed is:

1. A method for preventing adverse effects associated with the use of a medical device in a patient comprising introducing into the patient a medical device of which at least a portion comprises at least one of a sydnonimine and a furoxan.

2. The method of claim 1, wherein the method for preventing an adverse effect associated with the use of a medical device is a method for preventing or inhibiting platelet deposition.

3. The method of claim 1, wherein the method for preventing an adverse effect associated with the use of a medical device is a method for preventing thrombus formation.

4. The method of claim 1, wherein the method for preventing an adverse effect associated with the use of a medical device is a method for protecting or treating a damaged vascular surface.

5. The method of claim 1, wherein the at least one of a sydnonimine and a furoxan is present in a matrix coating on a surface of the medical device, wherein the matrix coating is nylon or plastic.

6. The method of claim 5, wherein the matrix coating provides for the intact release of the at least one of a sydnonimine and a furoxan.

7. The method of claim 6, wherein the matrix coating provides for the sustained release the at least one of a sydnonimine and a furoxan.

8. The method of claim 1, wherein the at least one of a sydnonimine and a furoxan is coated on a surface of the medical device.

9. The method of claim 1, wherein the at least one of a sydnonimine and a furoxan is directly or indirectly bound to reactive sites on a surface of the medical device.

10. The method of claim 1, wherein at least a portion of the medical device is formed of a polymer comprising the at least one of a sydnonimine and a furoxan, and wherein the polymer is nylon, polyethylene perthalate or polytetrafluoroethylene.

11. The method of claim 10, wherein the polymer provides for the release of the at least one of a sydnonimine and a furoxan.

12. The method of claim 10, wherein the polymer provides for the sustained release of the at least one of a sydnonimine and a furoxan.

13. The method of claim 10, wherein the polymer is biodegradable.

14. The method of claim 13, wherein the polymer is bioresorbable.

15. The method of claim 1, wherein the medical device comprises a catheter, a prosthetic heart valve, a synthetic vessel graft, a stent, an arteriovenous shunt or an artificial heart.

16. The method of claim 1, wherein at least a portion of the medical device comprises a sydnonimine.

17. The method of claim 1, wherein at least a portion of the medical device comprises a furoxan.

18. The method of claim 1, further comprising administering at least one of an anti-thrombogenic compound and a therapeutic agent.

19. The method of claim 18, wherein the anti-thrombogenic compound is heparin, hirudin, an analog of hirudin, warfarin, aspirin, indomethacin, dipyridamole, prostacyclin, prostaglandin-E, a sulfinpyrazone, a phenothiazine, a RGD peptide, a RGD peptide mimetic, an agent that blocks platelet glycoprotein IIb–IIIa receptors, ticlopidine or clopidogrel.

20. The method of claim 18, wherein the therapeutic agent is a monoclonal antibody, a fragment of recombinant human protein, a viral vector or an anti-sense molecule.

21. A method for preventing adverse effects associated with the use of a medical device in a patient comprising introducing into the patient a medical device during a medical procedure and before, during or after said procedure locally administering at least one of a sydnonimine and a furoxan to the site of contact of the medical device with any internal tissue.

22. The method of claim 21, wherein the method for preventing an adverse effect associated with the use of a medical device is a method for preventing or inhibiting platelet deposition.

23. The method of claim 21, wherein the method for preventing an adverse effect associated with the use of a medical device is a method for preventing thrombus formation.

24. The method of claim 21, wherein the method for preventing an adverse effect associated with the use of a medical device is a method for protecting or treating a damaged vascular surface.

25. The method of claim 21, wherein the at least one of a sydnonimine and a furoxan is administered through the lumen of an intraarterial or intravenous catheter.

26. The method of claim 21, comprising introducing into the patient a medical device during a medical procedure and before, during or after said procedure locally administering a sydnonimine to the site of contact of the medical device with any internal tissue.

27. The method of claim 21, comprising introducing into the patient a medical device during a medical procedure and before, during or after said procedure locally administering a furoxan to the site of contact of the medical device with any internal tissue.

28. The method of claim 21, further comprising administering at least one of an anti-thrombogenic compound and a therapeutic agent.

29. The method of claim 28, wherein the anti-thrombogenic compound is heparin, hirudin, an analog of hirudin, warfarin, aspirin, indomethacin, dipyridamole, prostacyclin, prostaglandin-E, a sulfinpyrazone, a phenothiazine, a RGD peptide, a RGD peptide mimetic, an agents that blocks platelet glycoprotein IIb–IIIa receptors, ticlopidine or clopidogrel.

30. The method of claim 28, wherein the therapeutic agent is a monoclonal antibody, a fragment of recombinant human protein, a viral vector or an anti-sense molecule.

31. A medical device comprising at least one of a sydnonimine and a furoxan.

32. The medical device of claim 31, wherein the medical device comprises a sydnonimine.

33. The medical device of claim 31, wherein the medical device comprises a furoxan.

34. The medical device of claim 31, further comprising at least one of an anti-thrombogenic compound and a therapeutic agent.

35. The medical device of claim 34, wherein the anti-thrombogenic compound is heparin, hirudin, an analog of hirudin, warfarin, aspirin, indomethacin, dipyridamole, prostacyclin, a prostaglandin-E, a sulfinpyrazone, a phenothiazine, a RGD peptide, a RGD peptide mimetic, an agent that blocks platelet glycoprotein IIb–IIIa receptors, ticlopidine or clopidogrel.

36. The method of claim 34, wherein the therapeutic agent is a monoclonal antibody, a fragment of recombinant human protein, a viral vector or an anti-sense molecule.

37. The medical device of claim 31, wherein the at least one of a sydnonimine and a furoxan is present in a matrix coating on a surface of the medical device, wherein the matrix coating is nylon or plastic.

38. The medical device of claim 37, wherein the matrix coating provides for intact release of the at least one of a sydnonimine and a furoxan.

39. The medical device of claim 37, wherein the matrix coating provides for the sustained release of the at least one of a sydnonimine and a furoxan.

40. The medical device of claim 31, wherein the at least one of a sydnonimine and a furoxan is coated on a surface of the medical device.

41. The medical device of claim 31, wherein the at least one of a sydnonimine and a furoxan is directly or indirectly bound to reactive sites on a surface of the medical device.

42. The medical device of claim 31, wherein at least a portion of the medical device is formed of a polymer comprising the at least one of a sydnonimine and a furoxan, wherein the polymer is nylon, polyethylene perthalate or polytetrafluoroethylene.

43. The medical device of claim 42, wherein the polymer provides the intact release of the at least one of a sydnonimine and a furoxan.

44. The medical device of claim 42, wherein the polymer provides for the sustained release of the at least one of a sydnonimine and a furoxan.

45. The medical device of claim 42, where the polymer is biodegradable.

46. The medical device of claim 45, wherein the polymer is bioresorbable.

47. The medical device of claim 31, wherein the medical device comprises a catheter, a prosthetic heart valve, a synthetic vessel graft, a stent, an arteriovenous shunt or an artificial heart.

48. A method for treating a damaged vessel in a patient in need thereof comprising introducing into the vessel at the site of damage the medical device of claim 31.

49. A method for preventing or inhibiting platelet deposition in a patient in need thereof comprising introducing into the patient the medical device of claim 31.

50. A method for preventing thrombus formation in a patient in need thereof comprising introducing into the patient the medical device of claim 31.

* * * * *